(12) United States Patent
Verkman et al.

(10) Patent No.: US 8,143,295 B2
(45) Date of Patent: Mar. 27, 2012

(54) COMPOUNDS HAVING ACTIVITY IN CORRECTING MUTANT-CFTR PROCESSING AND USES THEREOF

(75) Inventors: Alan Verkman, San Francisco, CA (US); Nicoletta Pedemonte, San Francisco, CA (US); Luis J. V. Galietta, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 875 days.

(21) Appl. No.: 11/908,591

(22) PCT Filed: Mar. 8, 2006

(86) PCT No.: PCT/US2006/008267
§ 371 (c)(1),
(2), (4) Date: Jul. 18, 2008

(87) PCT Pub. No.: WO2006/101740
PCT Pub. Date: Sep. 28, 2006

(65) Prior Publication Data
US 2008/0318984 A1 Dec. 25, 2008

Related U.S. Application Data

(60) Provisional application No. 60/663,501, filed on Mar. 18, 2005.

(51) Int. Cl.
*A01N 43/78* (2006.01)
(52) U.S. Cl. ........................................... 514/366
(58) Field of Classification Search .................. None
See application file for complete search history.

(56) References Cited

U.S. PATENT DOCUMENTS

| 4,501,750 A | 2/1985 | Sakano et al. |
| 6,770,663 B2 | 8/2004 | Wagle et al. |
| 2004/0198768 A1 | 10/2004 | Park Choo et al. |

FOREIGN PATENT DOCUMENTS

| EP | 0 519 449 A1 | 12/1992 |
| JP | 1009935 | 1/1989 |
| WO | 0144217 | 6/2001 |
| WO | 03004467 | 1/2003 |
| WO | 03106420 | 12/2003 |
| WO | 2004098510 | 11/2004 |
| WO | 2004/110352 A2 | 12/2004 |

OTHER PUBLICATIONS

U.S. Appl. No. 12/682,428, filed Apr. 2010, Kurth et al.*
Akihama et al., "Antiviral activities of benzothiazole derivatives," Chemical Abstracts Service, Database accession No. 1968:10369 (abstract).
Miller et al., "Anticoccidial Derivatives of 6-Azauracil. 2. High Potency and Long Plasma Life of N1-Phenyl Structures," Journal of Medicinal Chemistry (1979) vol. 22, No. 12, pp. 1483-1487.
Pedemonte et al., "Small-molecule correctors of defective deltaF508-CFTR cellular processing identified by high-throughput screening," Journal of Clinical Investigation (2005) vol. 115, No. 9, pp. 2564-2571.
European Search Report dated Oct. 13, 2010 for corresponding European Application No. 06737438.9.
Cormet-Boyaka et al., "Rescuing cystic fibrosis transmembrance conductance regulator (CFTR)-processing mutants by transcomplementation," PNAS, (May 25, 2004), vol. 101, No. 21, pp. 8221-8226.
International Search Report for International Application No. PCT/US06/08267.

* cited by examiner

*Primary Examiner* — Sreeni Padmanabhan
*Assistant Examiner* — Svetlana M Ivanova
(74) *Attorney, Agent, or Firm* — Carol L. Francis; Rudy J. Ng; Bozicevic, Field & Francis LLP

(57) ABSTRACT

The invention provides compositions, pharmaceutical preparations and methods for correcting cellular processing (e.g., folding, trafficking, or post-translational modification) of a mutant-cystic fibrosis transmembrane conductance regulator protein (e.g., ΔF508 CFTR) that are useful for the treatment of cystic fibrosis (CF). The compositions and pharmaceutical preparations of the invention may comprise one or more aminobenzothiazole-containing compounds, aminoarylthiazole-containing compounds, quinazolinylaminopyrimidinone-containing compounds, bisaminomethylbithiazole-containing compounds, or phenylaminoquino-line-containing compounds of the invention, or an analog or derivative thereof.

12 Claims, 11 Drawing Sheets

A.

B.

COMPOUNDS HAVING ACTIVITY IN CORRECTING MUTANT-CFTR PROCESSING AND USES THEREOF

STATEMENT REGARDING FEDERALLY SPONSORED RESEARCH

This invention was made with government support under grant nos. HL73856, EB00415, HL59198, EY13574, and DK35124 awarded by the National Institutes of Health. The government may have certain rights in this invention.

Work on this invention was also supported by grants from the Cystic Fibrosis Foundation and/or from Cystic Fibrosis Foundation Therapeutics.

BACKGROUND OF THE INVENTION

The cystic fibrosis transmembrane conductance regulator protein (CFTR) is a cAMP-activated chloride ($Cl^-$) channel expressed in epithelial cells in mammalian airways, intestine, pancreas and testis. CFTR is the chloride-channel responsible for cAMP-mediated $Cl^-$ secretion. Hormones, such as a β-adrenergic agonist, or toxins, such as cholera toxin, lead to an increase in cAMP, activation of cAMP-dependent protein kinase, and phosphorylation of the CFTR $Cl^-$ channel, which causes the channel to open. An increase in the concentration of $Ca^{2+}$ in a cell can also activate different apical membrane channels. Phosphorylation by protein kinase C can either open or shut $Cl^-$ channels in the apical membrane. CFTR is predominantly located in epithelia where it provides a pathway for the movement of $Cl^-$ ions across the apical membrane and a key point at which to regulate the rate of transepithelial salt and water transport. CFTR chloride channel function is associated with a wide spectrum of disease, including cystic fibrosis (CF) and with some forms of male infertility, polycystic kidney disease and secretory diarrhea.

The hereditary lethal disease CF is caused by mutations in the gene encoding the CFTR protein, a cAMP-activated $Cl^-$ channel expressed in airway, intestinal, pancreatic, and other secretory and absorptive epithelia. The principal clinical problem in CF is recurrent lung infections resulting in progressive deterioration in lung function. The most common CFTR mutation, deletion of phenylalanine-508 (ΔF508-CFTR), is present in at least one allele in about 90% of CF patients (Egan et al., (2004) *Science* 304:600-602). ΔF508-CFTR causes $Cl^-$ impermeability because it is not processed correctly, causing it to be retained at the endoplasmic reticulum (rather than the plasma membrane). ΔF508-CFTR also has reduced intrinsic $Cl^-$ conductance relative to wild type CFTR.

Strategies have been investigated to correct the defects in ΔF508-CFTR cellular processing and intrinsic function in cells. Cell growth at low temperature (<30° C.) (Denning et al., (1992) *Nature* 358, 761-764) or with high concentrations of chemical chaperones such as glycerol (Sato et al., (1996) J. Biol. Chem. 271, 635-638; Brown, et al., (1996) Cell Stress & Chaperones 1, 117-125) corrects partially defective ΔF508-CFTR cellular processing by a mechanism that may involve improved protein folding and stability (Sharma et al., (2001) J. Biol. Chem. 276, 8942-8950). A sustained increase in intracellular calcium concentration by thapsigargin also corrects defective ΔF508-CFTR processing (Egan et al., (2002) Nature Med. 8, 485-492), possibly by interfering with interactions with molecular chaperones. Compounds like phenylbutyrate facilitate ΔF508-CFTR cellular processing by altering chaperone function and/or transcriptional enhancement (Rubenstein et al., (2000) Am. J. Physiol. 278, C259-C267; Kang et al., (2002) Proc. Natl. Acad. Sci. U.S.A. 99, 838-843). Although these approaches provide insight into mechanisms of ΔF508-CFTR retention at the endoplasmic reticulum, they probably do not offer clinically-useful therapies.

ΔF508-CFTR has significantly impaired channel activity even when present at the cell plasma membrane (Dalemans et al., (1991) Nature 354, 526-528). Cell-attached patch-clamp measurements showed reduced ΔF508-CFTR open channel probability and prolonged closed times even with maximal cAMP stimulation (Haws et al., (1996) Am. J. Physiol. 270, C1544-C1555; Hwang et al., (1997) Am. J. Physiol. 273, C988-C998). Patch-clamp measurements in excised membranes indicated 7-fold reduced ΔF508-CFTR activation after phosphorylation compared to wildtype CFTR. Relatively high concentrations of the flavone genistein (>50 μM, Hwang, et al., (1997) Am. J. Physiol. 273, C988-C998; Wang et al., (2000) J. Physiol. 524, 637-638) or the xanthine isobutylmethylxanthine (>1 mM, Drumm et al., (1991) Science 254, 1797-1799) in combination with cAMP agonists increase ΔF508-CFTR channel activity. Again, these studies have not offered any clinically useful therapies.

There is accordingly still a need for compounds that can correct folding or cellular processing of a mutant CFTR, e.g., ΔF508-CTFR, and methods of using such compounds for the study and treatment of CF and the treatment and control of other secretory disorders. The present invention addresses these needs, as well as others.

SUMMARY OF THE INVENTION

The invention provides compositions, pharmaceutical preparations and methods for correcting cellular processing (e.g., folding, trafficking, or post-translational modification) of a mutant-cystic fibrosis transmembrane conductance regulator protein (e.g., ΔF508 CFTR) that are useful for the treatment of cystic fibrosis (CF). The compositions and pharmaceutical preparations of the invention may comprise one or more aminobenzothiazole-containing compounds, aminoarylthiazole-containing compounds, quinazolinylaminopyrimidinone-containing compounds, bisaminomethylbithiazole-containing compounds, or phenylaminoquinoline-containing compounds of the invention, or an analog or derivative thereof.

The invention provides for a pharmaceutical composition comprising a compound of formula (II):

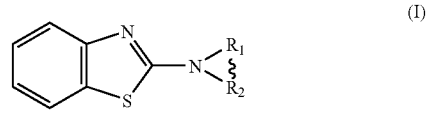

wherein $R_1$ is independently selected from a hydrogen, or a $C(=O \text{ or }=S)NH$ group fused to $R_2$, and $R_2$ is independently selected from a N=CH or N-alkyl linkage to a substituted or unsubstituted alkyl group, substituted or unsubstituted cycloalkyl group, or a substituted or unsubstituted aromatic ring, and a substituted or unsubstituted heteroaromatic ring; or a pharmaceutically acceptable derivative thereof, as an individual stereoisomer or a mixture thereof; or a pharmaceutically acceptable salt thereof. In one embodiment, the composition further includes at least one of a pharmaceutically acceptable carrier, a pharmaceutically acceptable diluent, a pharmaceutically acceptable excipient and a pharmaceutically acceptable adjuvant. In another embodiment, the composition does not contain detectable dimethyl sulfoxide.

In certain embodiments, $R_1$ of the composition is a hydrogen and the compound having formula (II) is a compound having formula (Ia):

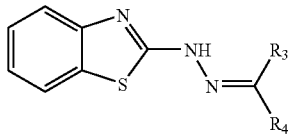

(Ia)

wherein $R_3$ is independently selected from a substituted or unsubstituted phenyl group and $R_4$ is a substituted or unsubstituted alkyl group. In one embodiments, $R_3$ is chosen from a 4-(methoxy)phenyl group, a 3-(nitro)phenyl group, a 4-(nitro)phenyl group, or a 4-(chloro)phenyl group. In another embodiment, $R_4$ is chosen from a hydrogen and a methyl group.

In other embodiments the compound is of formula (Ib):

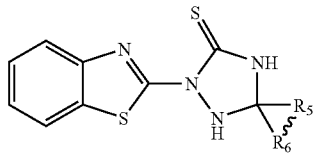

(Ib)

wherein $R_5$ and $R_6$ are selected from a substituted or unsubstituted alkyl group, or are a fused substituted or unsubstituted cycloalkyl ring group. In one embodiment, $R_5$ is an ethyl group. In another embodiment, $R_6$ is an ethyl group. In yet another embodiment, $R_5$ and $R_6$ are a fused tert(butyl)cyclohexane group.

In representative embodiments the compound is chosen from:

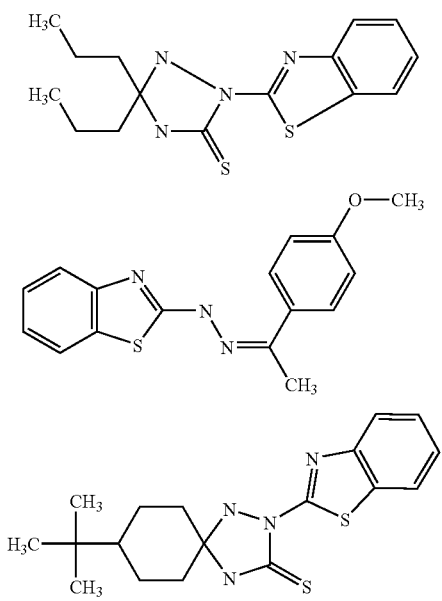

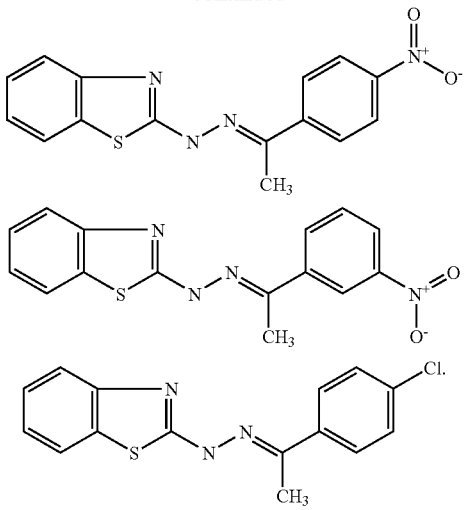

The invention also provides a pharmaceutical composition comprising a compound of formula (II):

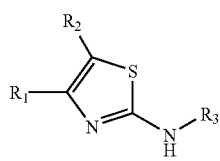

(II)

wherein $R_1$ is independently selected from a substituted or unsubstituted phenyl group, $R_2$ is independently selected from a hydrogen or an allyl group, $R_3$ is independently selected from a substituted or unsubstituted phenyl group, a substituted or unsubstituted heteroaromatic group, a substituted amino group, a substituted acyl group; or a pharmaceutically acceptable derivative thereof, as an individual stereoisomer or a mixture thereof; or a pharmaceutically acceptable salt thereof. In one embodiment, the composition further comprises at least one of a pharmaceutically acceptable carrier, a pharmaceutically acceptable diluent, a pharmaceutically acceptable excipient and a pharmaceutically acceptable adjuvant. In another embodiment, the composition does not contain detectable dimethyl sulfoxide.

In one embodiment, $R_1$ is chosen from an unsubstituted phenyl group, a unsubstituted biphenyl group, a 3-, 4-di(methyl)phenyl group, a 4-(methyl)phenyl group, a 3-, 4-di(methoxy)phenyl group, a 3-, 4-di(hydroxy)phenyl group, a 4-(bromo)phenyl group, a 4-(propene)phenyl group, a 3-(methyl) 4-(methoxy)phenyl group, or a 3-(nitro)-4(methyl)phenyl group. In another embodiment, $R_2$ is chosen from a hydrogen or a methyl group. In yet another embodiment, $R_3$ is chosen from a unsubstituted phenyl group, as a 3-(chloro) phenyl group, a 4-(fluoro)phenyl group, a 2-(methyl)phenyl group, a 2-(ethoxy)phenyl group, a 2-,5-di(methoxy)-4-(chloro)phenyl group, a 4-(acetamide)phenyl group, a unsubstituted pyrimidine group, a 3-(methyl)pyridine group, a di(methyl)butylideneamine group, an acyl-thiophene group, an acyl(4-t-butyl-phenyl) group, or an acyl-methylthio-imidazol-5-phenyl group. In representative embodiments, the compound is chosen from:

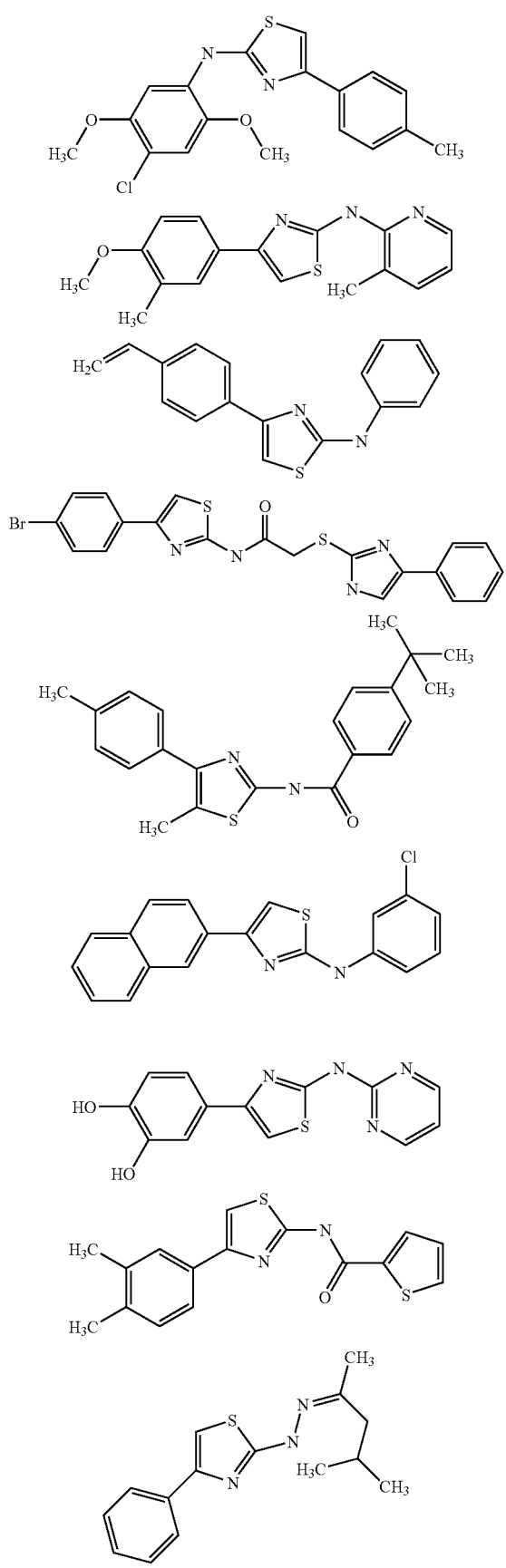
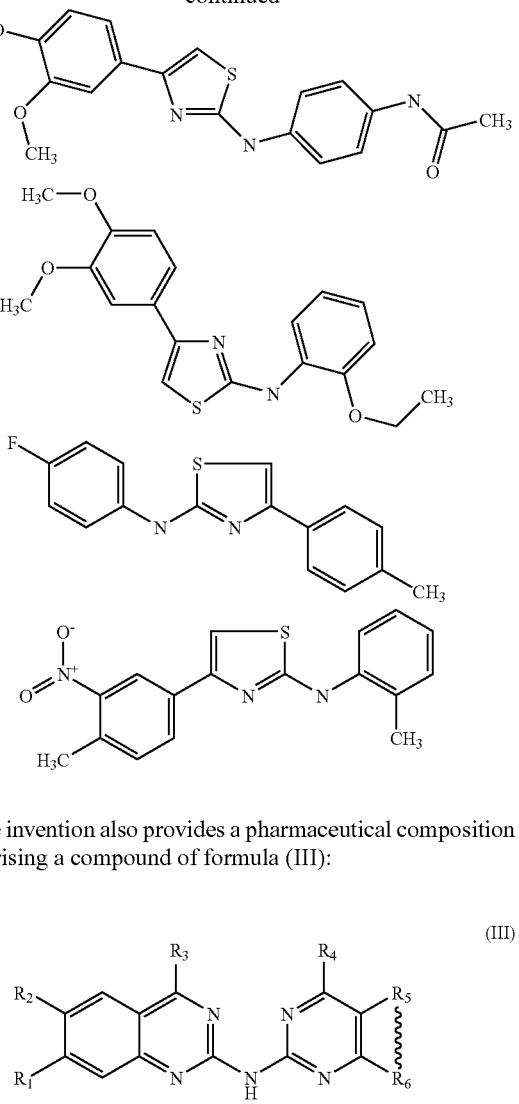

The invention also provides a pharmaceutical composition comprising a compound of formula (III):

(III)

wherein $R_1$ is chosen from a hydrogen, an alkyl group, or an alkoxy group; $R_2$ is chosen from a hydrogen, an alkyl group, or an alkoxy group; $R_3$ is an alkyl group; $R_4$ is chosen from a hydroxyl group or a carbonyl group; $R_5$ and $R_6$ are chosen from a fused cycloalkyl group, a hydrogen, an alkyl group, or a substituted or unsubstituted phenyl group; or a pharmaceutically acceptable derivative thereof, as an individual stereoisomer or a mixture thereof, or a pharmaceutically acceptable salt thereof. In one embodiment, the composition further includes at least one of a pharmaceutically acceptable carrier, a pharmaceutically acceptable diluent, a pharmaceutically acceptable excipient and a pharmaceutically acceptable adjuvant. In another embodiment, the composition does not contain detectable dimethyl sulfoxide.

In one embodiment, $R_1$ chosen from a hydrogen, a methyl group, an ethyl group, a methoxy group, or an ethoxy group. In another embodiment, $R_2$ is chosen from a hydrogen, a methyl group, an ethyl group, a methoxy group, or an ethoxy group. In yet another embodiment, $R_3$ is chosen from a methyl group or an ethyl group. In yet another embodiment, $R_4$ is chosen from a hydroxyl group or a carbonyl group. In yet another embodiment, $R_5$ is chosen from a hydrogen, a methyl group, an ethyl group, a unsubstituted phenyl group, or a 2-methylthio-1H-benzoimidazole group. In yet another embodiment, $R_6$ is chosen from a hydrogen, a methyl group, an ethyl group, a unsubstituted phenyl group, or a 2-methylthio-1H-benzoimidazole group. In yet another embodiment, $R_5$ and $R_6$ are a fused cyclopenyl group. In representative embodiments, the compound is chosen from:

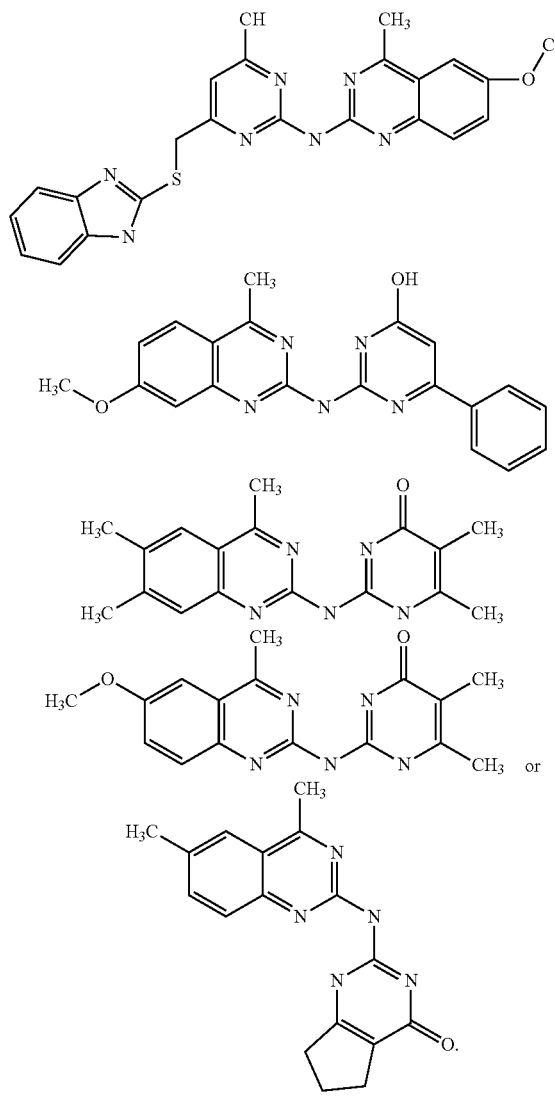

The invention also provides a pharmaceutical composition comprising a compound of formula (IV):

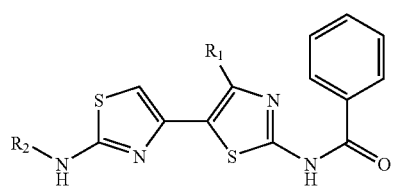

(IV)

wherein $R_1$ is a alkyl group and $R_2$ is a substituted or unsubstituted phenyl group; or a substituted or unsubstituted phenyl group; or a pharmaceutically acceptable derivative thereof, as an individual stereoisomer or a mixture thereof; or a pharmaceutically acceptable salt thereof. In one embodiment, the composition further includes at least one of a pharmaceutically acceptable carrier, a pharmaceutically acceptable diluent, a pharmaceutically acceptable excipient and a pharmaceutically acceptable adjuvant. In another embodiment, the composition does not contain detectable dimethyl sulfoxide.

In one embodiment, $R_1$ is a methyl group. In another embodiment, $R_2$ is chosen from a 3-(nitro)phenyl group, a 2-methoxyphenyl, a 2-ethoxyphenyl, a 1-phenylethyl-1-one group, or a 3-chloro-6-methoxyphenyl group. In representative embodiments, the compound is chosen from:

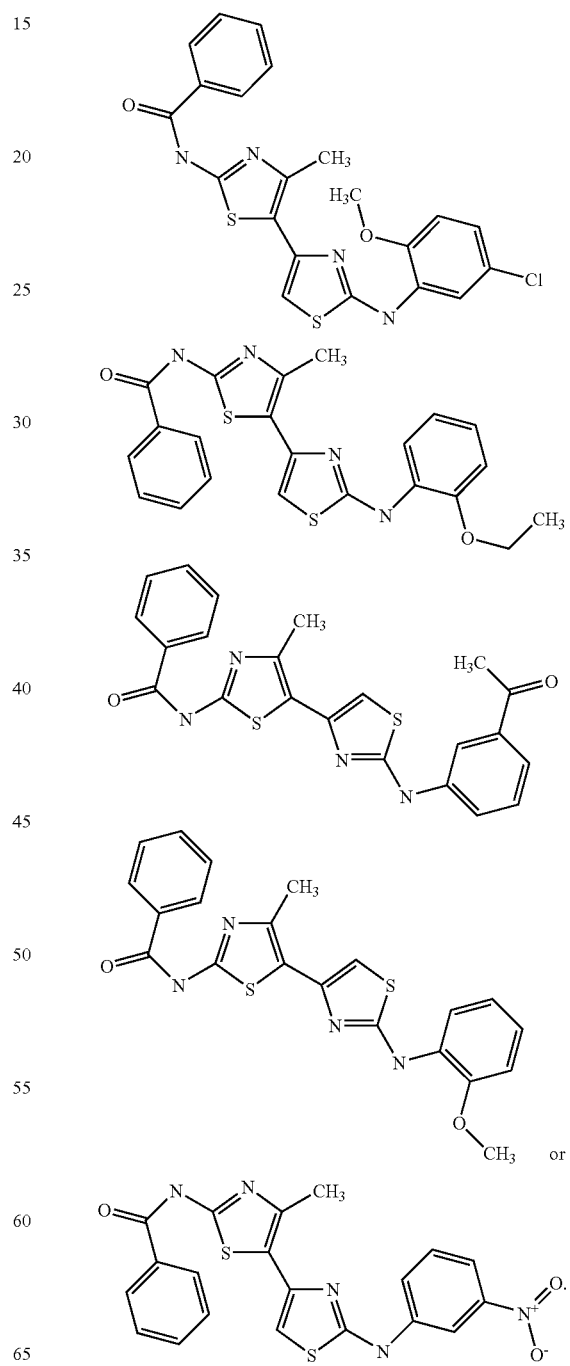

The invention also provides a pharmaceutical composition comprising a compound of formula (V):

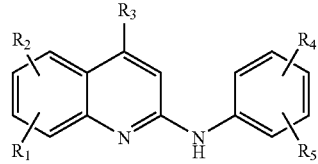

wherein $R_1$ is chosen from a hydrogen, or an alkyl group; $R_2$ is chosen from a hydrogen, or an alkyl group; $R_3$ is an alkyl group; $R_4$ is chosen from a hydrogen, an alkyl group, an alkoxy group, or a halogen group; and $R_5$ is chosen from a hydrogen, an alkyl group, an alkoxy group, or a halogen group; or a pharmaceutically acceptable derivative thereof, as an individual stereoisomer or a mixture thereof; or a pharmaceutically acceptable salt thereof. In one embodiment, the composition further includes at least one of a pharmaceutically acceptable carrier, a pharmaceutically acceptable diluent, a pharmaceutically acceptable excipient and a pharmaceutically acceptable adjuvant. In another embodiment, the composition does not contain detectable dimethyl sulfoxide.

In one embodiment, $R_1$ is chosen from a hydrogen or a methyl group. In another embodiment, $R_2$ is chosen from a hydrogen or a methyl group. In yet another embodiment, $R_3$ is chosen from a hydrogen or a methyl group. In yet another embodiment, $R_4$ is chosen from a hydrogen, a brominde group, a chloride group, or a methoxyl group. In yet another embodiment, $R_5$ is chosen from a hydrogen, a brominde group, a chloride group, or a methoxyl group. In representative embodiments, the compound is chosen from:

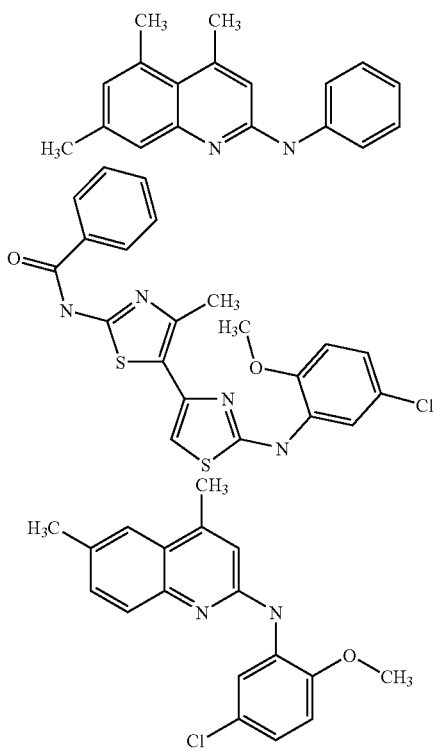

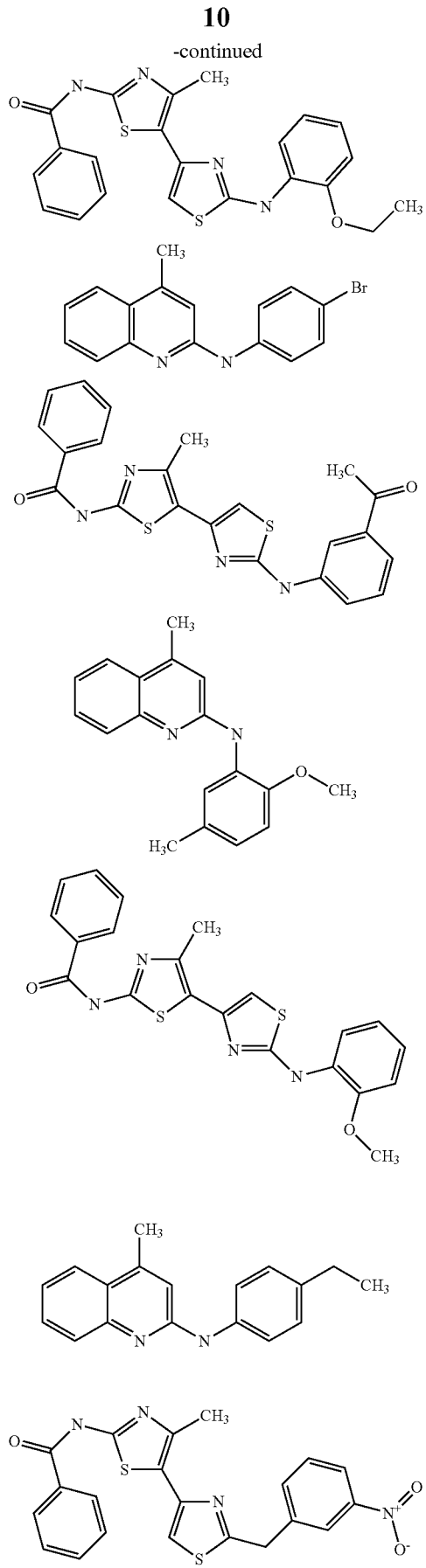

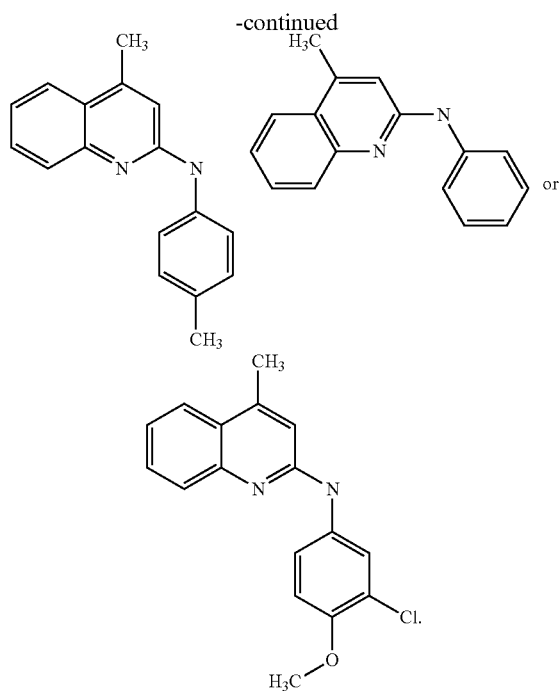

The invention also provides for a method of treating a subject having a condition associated with mutant-CFTR, said method comprising administering to the subject a therapeutically effective amount of a compound selected from the compounds of the present invention. In some embodiments, the condition is cystic fibrosis. In some embodiments, the subject, after treatment, has a decrease in mucous or bacterial titer in their lungs, a decrease in coughing or wheezing, a decrease in pancreatic insufficiency, or a decrease in electrolyte levels in their sweat. In some embodiments, the subject is a non-human animal. In embodiments of particular interest, the animal is a mammal. In some embodiments, the mutant-CFTR is a ΔF508-CFTR.

The invention also provides for a method of increasing ion permeability of a cell producing a mutant-CFTR protein, the method including contacting the cell with an effective amount of compound of the present invention, the contacting being effective to increase CFTR-mediated ion permeability of said cell. In some embodiments, the cell contains a recombinant expression cassette that encodes said mutant-CFTR protein. In other embodiments, the contains a genome that encodes said mutant-CFTR protein. In yet other embodiments, the mutant-CFTR is a ΔF508-CFTR.

The invention also provides for a method of treating a subject having a condition associated with mutant-CFTR, the method including administering to the subject a therapeutically effective amount of a compound selected from the compounds of the present invention. In some embodiments, the condition is cystic fibrosis. In some embodiments the subject, after treatment, has a decrease in mucous or bacterial titer in their lungs, a decrease in coughing or wheezing, a decrease in pancreatic insufficiency, or a decrease in electrolyte levels in their sweat. In some embodiments the subject is a non-human animal. In embodiments of particular interest the animal is a mammal. In some embodiments the mutant-CFTR is ΔF508-CFTR.

The invention also provides for a method of increasing ion permeability of a cell producing a mutant-CFTR protein, the method including contacting the cell with a compound in an amount effective to increase ion permeability of said cell, wherein the compound is selected from the compounds of the present invention. In some embodiments the cell contains a recombinant expression cassette that encodes said mutant-CFTR protein. In other embodiments the cell contains a genome that encodes said mutant-CFTR protein. In yet other embodiments the ion permeability increases an ion transporting activity that increases a rate of transport of ions across the plasma membrane of said cell. In yet other embodiments the mutant-CFTR is ΔF508-CFTR.

These and other objects and advantages of the invention will be apparent from the detailed description below.

BRIEF DESCRIPTION OF THE DRAWINGS

The invention will be more fully understood by reference to the following drawings, which are for illustrative purposes only.

Figure 1:
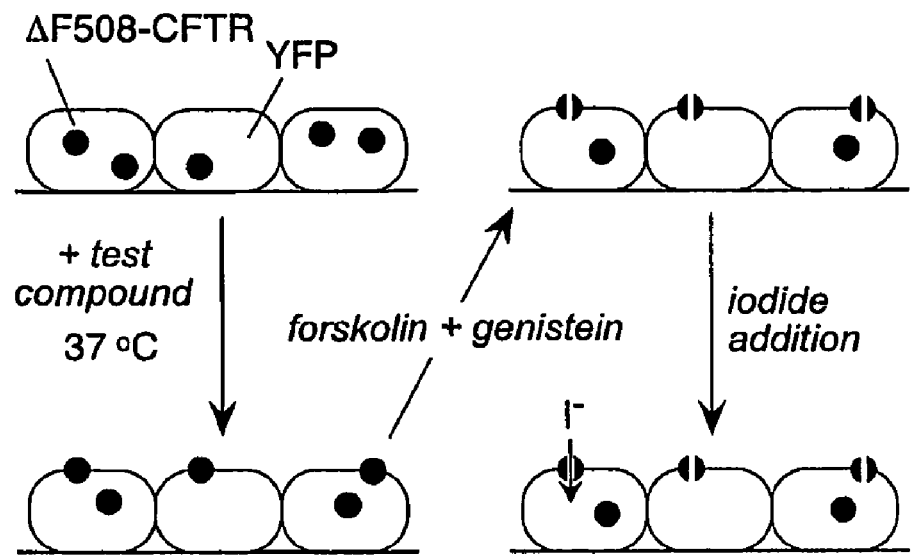
FIG. 1 shows a schematic of the subject screening procedure. FRT cells coexpressing ΔF508-CFTR and a halide-sensitive YFP were incubated with test compounds (10 μM) at 37° C. ΔF508-CFTR function was assayed at 18-24 hours in a plate reader by YFP fluorescence quenching by iodide in the presence of forskolin (20 μM)+genistein (50 μM).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a compound" includes a plurality of such compounds and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The invention provides compositions, pharmaceutical preparations and methods which find at least one use in the context of treating a subject having a mutant cystic fibrosis transmembrane conductance regulator (CFTR) protein, particularly where the mutation in the CFTR is associated with cellular mis-processing (e.g., folding, trafficking, or post-translational modification) of the CFTR. An example of such a mutant CFTR is the ΔF508 CFTR. Without being held to theory, the compounds and methods of the invention provide for "correction" of such cellular mis-processing of such a mutant CFTR protein that are useful for the treatment of cystic fibrosis (CF).

In general, the compositions and pharmaceutical preparations of the invention comprise one or more nitrogen-containing heteroaromatic compounds, with aminobenzothiazole-containing compounds, aminoarylthiazole-containing compounds, quinazolinylaminopyrimidinone-containing compounds, bisaminomethylbithiazole-containing compounds, and phenylaminoquinoline-containing compounds, including analogs or derivatives thereof, being of particular interest.

Definitions

A "mutant cystic fibrosis transmembrane conductance regulator protein", or "mutant-CFTR" is the protein that results from a mutation, e.g., deletion mutation, insertion mutation, or point (substitution) mutation of the CFTR gene product relative to wildtype. As used herein a "mutant cystic fibrosis transmembrane conductance regulator protein", or "mutant-CFTR" is dysfunctional as compared to a functional (e.g., wildtype) CFTR where the dysfunction can encompass one or more of the following: (i) aberrant CFTR production (e.g., at the level of transcription or translation); (ii) aberrant folding and/or trafficking; (iii) abnormal regulation of conductance; (iv) decreases in chloride conductance; (v) reduction in synthesis; and the like. A "mutant-CFTR gene" is a gene, or coding sequence, which encodes a mutant-CFTR.

For the purposes of this application, the terms "genome" and "gene" are used interchangeably, e.g. "genome that encodes mutant-CFTR" and "gene that encodes mutant-CFTR".

A "gating defective mutant cystic fibrosis transmembrane conductance regulator protein", or "gating defective mutant-CFTR" is a mutant-CFTR that is present on the cell surface and is defective in gating of ions through the channel (e.g., regulation of ion transport). Thus, as used herein a "gating defective mutant-CFTR" encompasses dysfunctions associated with (i) abnormal regulation of conductance; and or (ii) decreases in chloride conductance.

A "mutant-CFTR protein-mediated condition" means any condition, disorder or disease, or symptom of such condition, disorder, or disease, that results from or is correlated to the presence of a mutant-CFTR, e.g., ΔF508-CFTR, e.g., chloride ion impermeability caused by reduced activity of ΔF508-CFTR in ion transport relative to a wild-type CFTR. A "mutant-CFTR protein-mediated condition" encompasses conditions in an affected subject which are associated with the presence of a ΔF508-CFTR mutation on at least one allele, thus including subjects that carry a ΔF508-CFTR mutation on both alleles as well as compound heterozygous subjects having two different mutant forms of CFTR, e.g., a subject with one copy of ΔF508-CFTR and a copy of different mutant form of CFTR.

Such conditions, disorders, diseases, or symptoms thereof are treatable by specific activation of mutant-CFTR activity, e.g., activation of mutant-CFTR ion transport. ΔF508-CFTR is correlated to the presence of cystic fibrosis (CF), and a description of this disease, including its symptoms, is found in Accession No. 602421 (entitled cystic fibrosis transmembrane conductance regulator; CFTR), and Accession No. 219700 (entitled Cystic fibrosis; CF) of the Online Mendelian Inheritance of Man database, as found at the world wide website of the National Institute of Health at ncbi.nlm.nih.gov. Symptoms of mutant-CFTR protein-mediated conditions include meconium ileus, liver disease including biliary tract obstruction and stenosis, pancreatic insufficiency, pulmonary disease including chronic *Pseudomonas aeruginosa* infections and other infections of the lung, infertility associated with abnormal vas deferens development or abnormal cervical mucus, and carcinoma including adenocarcinoma. Many subjects that have a mutant-CFTR protein-mediated condition are homozygous for a gene encoding a ΔF508-CFTR protein.

A "ΔF508-cystic fibrosis transmembrane conductance regulator protein", or "ΔF508-CFTR" is the protein that results from the deletion of a phenylalanine residue at amino acid position 508 of the CFTR gene product. A "ΔF508-CFTR gene" is a gene, or coding sequence, which encodes ΔF508-CFTR. A ΔF508-CFTR gene usually results from deletion of three nucleotides corresponding to the phenylalanine residue at amino acid position 508 of the encoded CFTR gene product. For the purposes of this application, the terms "genome" and "gene" are used interchangeably, e.g. "genome that encodes ΔF508-CFTR" and "gene that encodes ΔF508-CFTR". For an example of a gene that encodes ΔF508-CFTR, see, e.g. WO 91/02796.

A "mutant-CFTR activator" as used herein is a compound that increases the level of ion transport by a mutant-CFTR relative to ion transport in the absence of the compound, and particularly with respect to transport of chloride ions. CFTR activators of the invention of particular interest are those that are specific mutant-CFMR activators, e.g., compounds that activate mutant-CFTR activity rather than affecting CFTR cellular misprocessing. Mutant-CFTR activators are usually high-affinity mutant-CFTR activators, e.g., have an affinity for mutant-CFTR of at least about one micromolar, about one to five micromolar, about 200 nanomolar to one micromolar, about 50 nanomolar to 200 nanomolar, or below 50 nanomolar.

A "gating defective mutant-CFTR activator" as used herein is a compound that increases the level of ion transport by a gating defective mutant-CFTR relative to ion transport in the absence of the compound, and particularly with respect to transport of chloride ions. CFTR activators of the invention of particular interest are those that are specific gating defective mutant-CFTR activators, e.g., compounds that activate gating defective mutant-CFTR activity rather than affecting, for example, CFTR cellular misprocessing. Gating defective mutant-CFTR activators are usually high-affinity activators of gating defective mutant-CFTRs, e.g., have an affinity for a gating defective mutant-CFTR (e.g., ΔF508-CFTR, G551D-CFTR, G1349D-CFTR, or D1152H-CFTR) of at least about one micromolar, about one to five micromolar, about 200 nanomolar to one micromolar, about 50 nanomolar to 200 nanomolar, or below 50 nanomolar.

A "ΔF508-CFTR activator" as used herein is a compound that increases the level of ion transport by ΔF508-CFTR relative to ion transport in the absence of the compound, and particularly with respect to transport of chloride ions. CFTR activators of the invention of particular interest are those that are specific ΔF508-CFTR activators, e.g., compounds that activate ΔF508-CFTR activity rather than affecting CFTR cellular misprocessing. ΔF508-CFTR activators are usually high-affinity ΔF508-CFTR activators, e.g., have an affinity for ΔF508-CFTR of at least about one micromolar, about one to five micromolar, about 200 nanomolar to one micromolar, about 50 nanomolar to 200 nanomolar, or below 50 nanomolar.

As used herein and in the cystic fibrosis field a "mutant CFTR potentiator" refers to a compound that increases a basal level of ion transport by a mutant-CFTR (e.g, ΔF508CFTR, G551D-CFTR, G1349D-CFTR, or D1152H-CFTR), where the mutant CFTR (in the absence of the compound) exhibits aberrantly low levels of ion transport relative to wildtype CFTR. As such, a "mutant-CFTR potentiator" refers to a potentiator compound that, provides for increased level of ion transport by a mutant-CFTR relative to ion transport capability of the mutant-CFTR in the absence of the compounds.

As used herein and in the cystic fibrosis field a "mutant-CFTR corrector" is a compound that increases the level of ion transport by a mutant-CFTR relative to ion transport in the absence of the compound by correcting the underlying defect of the CFTR polypeptide, e.g., a defect that results from post-translational processing (e.g., folding, trafficking, or post-translation modification, such as post-translational glycosylation). CFTR correctors of the invention of particular interest are those that facilitate correction of specific mutant-CFTRs. Mutant-CFTR correctors are usually exhibit high-affinity for one or more mutant-CFTRs, e.g., have an affinity for mutant-CFTR of at least about one micromolar, about one to five micromolar, about 200 nanomolar to one micromolar, about 50 nanomolar to 200 nanomolar, or below 50 nanomolar.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

The term "isolated compound" means a compound which has been substantially separated from, or enriched relative to, other compounds with which it occurs in nature. Isolated compounds are usually at least about 80%, more usually at least 90% pure, even more preferably at least 98% pure, most preferably at least about 99% pure, by weight. The present invention is meant to comprehend diastereomers as well as their racemic and resolved, enantiomerically pure forms and pharmaceutically acceptable salts thereof.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient to effect such treatment for the disease. The "therapeutically effective amount" will vary depending on the compound, the disease and its severity and the age, weight, etc., of the subject to be treated.

The terms "subject" and "patient" mean a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human animals having commercial importance (e.g., livestock and domesticated animals) are of particular interest.

"Mammal" means a member or members of any mammalian species, and includes, by way of example, canines; felines; equines; bovines; ovines; rodentia, etc. and primates, particularly humans. Non-human animal models, particularly mammals, e.g. primate, murine, lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, using a penetration enhancer other than DMSO. In other embodiments, the pharmaceutical compositions are suitable for administration by a route other than transdermal administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobronic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, allynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C=C(OR) where R is hydrogen, alkyl, alkenyl, alkynyl, aryl, heteroaryl, aralkyl, heteroaralkyl, cycloalkyl or heterocyclyl.

A "pharmaceutically acceptable enol ester" of a compound of the invention means an enol ester that is pharmaceutically acceptable and that possesses the desired pharmacological activity of the parent compound, and includes, but is not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Pro-drugs" means any compound that releases an active parent drug according to formula (I) in vivo when such pro-drug is administered to a mammalian subject. Prodrugs of a compound of formula (I) are prepared by modifying functional groups present in the compound of formula (I). in such a way that the modifications may be cleaved in vivo to release the parent compound. Prodrugs include compounds of formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of formula (I), and the like.

The term "organic group" and "organic radical" as used herein means any carbon-containing group, including hydrocarbon groups that are classified as an aliphatic group, cyclic group, aromatic group, functionalized derivatives thereof and/or various combination thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an allyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the allyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2,3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl) n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)allyl, phenyl, substituted phenyl, phenylalkyl, and (substituted phenyl)allyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature or element may, but need not, occur, and that the description includes instances where the event or circumstance occurs and instances in which it does not. For example, "heterocyclo group optionally mono- or di-substituted with an alkyl group" means that the allyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Overview

The invention is based on the discovery of compounds that increase ion transport in a mutant-cystic fibrosis transmembrane conductance regulator protein (mutant-CFTR), e.g., ΔF508-CFTR. Such compounds find use in methods of treatment of mutant-CFTR-mediated diseases and conditions, e.g., cystic fibrosis (CF). Such compounds also find use in the study of CFTR ion transport, particularly that of ΔF568-CFTR.

In one embodiment, the invention provides high-affinity small-molecule compounds that correct cellular processing (e.g., folding, trafficking, or post-translational modification) of a mutant-cystic fibrosis transmembrane conductance regulator protein (e.g., ΔF508 CFTR). The compounds contemplated by the invention include the following structural classes: (1) aminobenzothiazole containing compounds; (2) aminoarylthiazole containing compounds; (3) quinazolinylaminopyrimidinone containing compounds; (4) bisaminomethylbithiazole containing compounds; and (5) phenylaminoquinoline containing compounds.

The discovery of the subject compounds was based on screening of numerous candidate compounds using an assay designed to identify compounds that correct cellular processing (e.g., folding or trafficking) of mutant-CFTR. A screening of 150,000 chemically diverse compounds identified several compounds and analogs as effective mutant-CFTR potentiators. The subject compounds are unrelated chemically and structurally to previously known compounds that increase activity of mutant-CFTR.

The compositions and methods of the invention will now be described in more detail.

Compositions

2-Aminobenzothiazole Containing Compounds

In certain embodiments, the corrector compound of the present invention is a 2-aminobenzothiazole containing compounds described herein, which comprises a substituted aminobenzothiazole group. In specific embodiments, the subject compound are generally described by Formula (I) as follows:

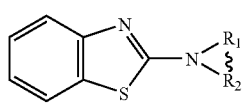
(I)

wherein $R_1$ is independently selected from a hydrogen, or a C(=O or =S)NH group fused to $R_2$, and $R_2$ is independently selected from a N=CH or N-alkyl linkage to a substituted or unsubstituted alkyl group, substituted or unsubstituted cycloalkyl group, or a substituted or unsubstituted aromatic ring, and a substituted or unsubstituted heteroaromatic ring, or a pharmaceutically acceptable derivative thereof, as an individual steroisomer or a mixture thereof. Exemplary substitutions for $R_1$ and $R_2$ are described in more detail below.

In certain embodiments, the 2-aminobenzothiazole containing compounds are generally described by Formula (I), wherein $R_1$ is a hydrogen. Such compounds are generally described by Formula (Ia):

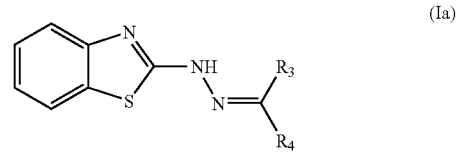
(Ia)

wherein $R_3$ is independently selected from a substituted or unsubstituted phenyl group and $R_4$ is an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or a pharmaceutically acceptable derivative thereof, as an individual stereoisomer or a mixture thereof. Exemplary substitutions for $R_3$ and $R_4$ are described in more detail below.

In some embodiments, $R_3$ is independently chosen from an unsubstituted phenyl group, a unsubstituted biphenyl group, or a substituted phenyl group, such as a mono- or di-(alkyl)phenyl, a mono- or di-(alkoxy)phenyl, a mono- or di-(hydroxy)phenyl, a mono- or di-(halo)phenyl, a mono- or di-(alkenyl)phenyl, a mono- or di-(nitro)phenyl, a mono(alkyl)-mono(alkoxy)phenyl, a di(alkoxy)-mono(halo)phenyl, and a mono(nitro)-mono(allyl)phenyl; and $R_4$ is independently selected from a hydrogen and a lower alkyl group, such as a methyl group and an ethyl group.

In representative embodiments, $R_3$ is independently selected from a mono-(alkoxy)phenyl group such as a 4-(methoxy)phenyl, a mono-(nitro)phenyl group such as a 3-(nitro)phenyl group or a 4-(nitro)phenyl group, or a mono (halo)phenyl group, such as a 4-(chloro)phenyl group, and $R_4$ is independently selected from a hydrogen and a lower alkyl group such as a methyl group and an ethyl group.

In certain embodiments, the 2-aminobenzothiazole containing compounds are generally described by Formula (I), wherein $R_1$ and $R_2$ are a fused thione substituted triazolidine ring having an $R_5$ group and an $R_6$ group. Such compounds are generally described by Formula (Ib):

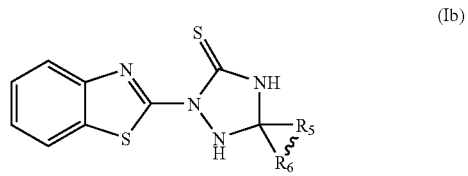
(Ib)

wherein $R_5$ and $R_6$ are independently selected from a substituted or unsubstituted alkyl group such as such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or a substituted or unsubstituted cycloalkyl ring, or a pharmaceutically acceptable derivative thereof, as an individual stereoisomer or a mixture thereof. Exemplary substitutions for $R_5$ and $R_6$ are described in more detail below.

In some embodiments, $R_5$ is a lower alkyl group (e.g., $C_1$-$C_4$) such as a methyl group and an ethyl group and $R_6$ is a lower alkyl group (e.g., $C_1$-$C_4$) such as a methyl group and an ethyl group. In other embodiments, $R_5$ and $R_6$ are a substituted or unsubstituted cycloalkyl group, such as a (alkyl) cycloalkyl group, such as a tert(butyl)cyclohexane group.

In some embodiments of the invention, the 2-aminobenzothiazole containing compounds may comprise a formula of the following:

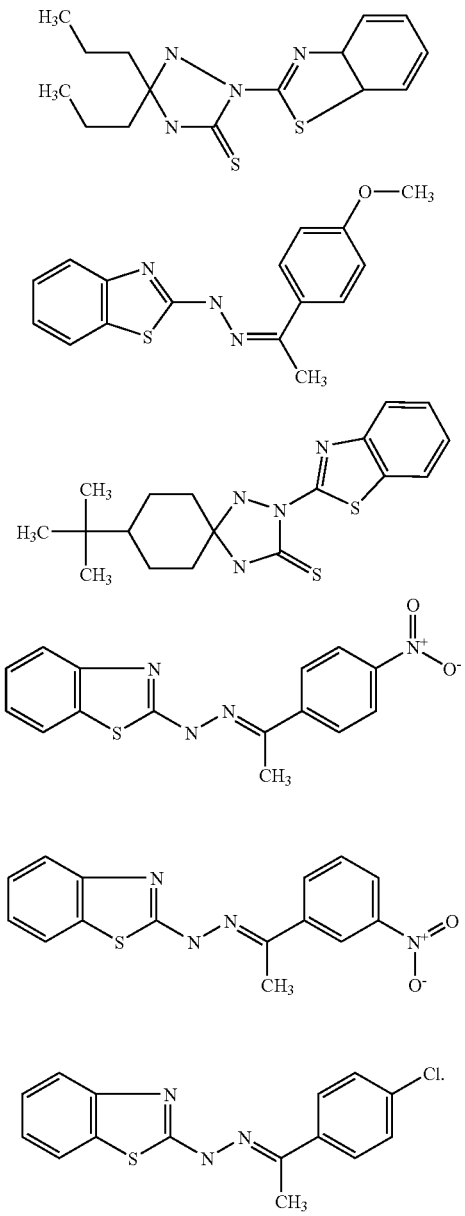

2-Amino-4-Arylthiazole Containing Compounds

In certain embodiments, the corrector compound of the present invention is a 2-Amino-4-Arylthiazole containing compounds described herein, which comprises a amino substituted arylthiazole group. In specific embodiments, the subject compound are generally described by Formula (II) as follows:

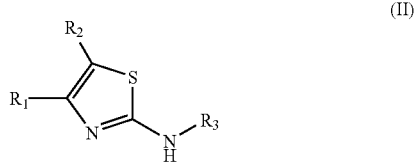

wherein $R_1$ is independently selected from a substituted or unsubstituted phenyl group; $R_2$ is independently selected from a hydrogen and an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $R_3$ is independently selected from a substituted or unsubstituted phenyl group, a substituted or unsubstituted heteroaromatic group, a substituted amino group, a substituted keto group; or a pharmaceutically acceptable derivative thereof, as an individual stereoisomer or a mixture thereof. Exemplary substitutions for $R_1$, $R_2$, and $R_3$ are described in more detail below.

In certain embodiments, $R_1$ is independently chosen from an unsubstituted phenyl group, a unsubstituted biphenyl group, or a substituted phenyl group, such as a mono- or di-(alkyl)phenyl, a mono- or di-(alkoxy)phenyl, a mono- or di-(hydroxy)phenyl, a mono- or di-(halo) phenyl, a mono- or di-(alkenyl)phenyl, a mono- or di-(nitro)phenyl, a mono (alkyl)-mono(alkoxy)phenyl, a di(alkoxy)-mono(halo)phenyl, and a mono(nitro)-mono(alkyl)phenyl; $R_2$ is independently selected from a hydrogen and a lower alkyl group (e.g., $C_1$-$C_4$), such as a methyl group and an ethyl group; $R_3$ is independently selected from a unsubstituted phenyl group, a substituted phenyl group such as a mono- or di-(halo)phenyl, a mono- or di-(alkyl)phenyl, a mono- or di-(alkoxy)phenyl, a mono(amide)phenyl, or a mono- or di-(alkoxy)-mono- or di-halo)phenyl, a unsubstituted heteroaromatic group such as a pyrimidine, a substituted heteroaromatic group such as a mono- or di-(alkyl)pyrimidine, a substituted amino group such as a mono(alkenyl)amino, and an acyl group such as an acyl-thiophene group, an acyl unsubstituted phenyl group, a substituted phenyl group such as a mono- or di-(halo)phenyl, a mono- or di-(alkyl)phenyl, a mono- or di-(alkoxy)phenyl, a mono(amide)phenyl, or a mono- or di-(alkoxy)-mono- or di-(halo)phenyl group, or an acyl alkylthio-imidazol-(5-unsubstituted phenyl group, a substituted phenyl group such as a mono- or di-(halo)phenyl, a mono- or di-(alkyl)phenyl, a mono- or di-(alkoxy)phenyl, a mono(amide)phenyl, or a mono- or di-(alkoxy)-mono- or di-(halo)phenyl group or a pharmaceutically acceptable derivative thereof, as an individual stereoisomer or a mixture thereof, In representative embodiments, $R_1$ is independently chosen from an unsubstituted phenyl group, a unsubstituted biphenyl group, a di-(methyl)phenyl group such as a 3-, 4-di (methyl)phenyl group, a mono-(methyl)phenyl group such as a 4-(methyl)phenyl group, a di-(methoxy)phenyl group such as a 3-, 4-di(methoxy)phenyl group, a di-(hydroxy)phenyl group such as a 3-, 4-di(hydroxy)phenyl group, a mono-(bromo)phenyl group such as a 4-(bromo)phenyl group, a mono-(propene)phenyl group such as a 4-(propene)phenyl group, a mono(methyl)-mono(methoxy)phenyl group such as a 3-(methyl)-4-(methoxy)phenyl group, and a mono(nitro)-mono(methyl)phenyl group such as a 3-(nitro)-4(methyl) phenyl group; and $R_2$ is independently selected from a hydrogen and a methyl group.

In representative embodiments $R_3$ is independently selected from a unsubstituted phenyl group, a mono-(chloro)

phenyl group such as a 3-(chloro)phenyl group, a mono-(fluoro)phenyl group such as a 4-(fluoro)phenyl group, a mono-(methyl)phenyl group such as a 2-(methyl)phenyl group, a mono-(ethoxy)phenyl group such as a 2-(ethoxy)phenyl group, a di(methoxy)-mono(chloro)phenyl group such as a 2-,5-di(methoxy)-4-(chloro)phenyl group, a mono-(acetamide)phenyl group such as a 4-(acetamide)phenyl group, an unsubstituted pyrimidine group, a mono-(methyl)pyridine group such as a 3-(methyl)pyridine group, a di(m-ethyl)butylideneamine group, an acyl thiophene group, an acyl (4-t-butyl-phenyl) group or an acyl methylthio-imidazol-5-phenyl group.

In some embodiments of the invention, the 2-amino-4-arylthiozole containing compounds may comprise a formula of the following:

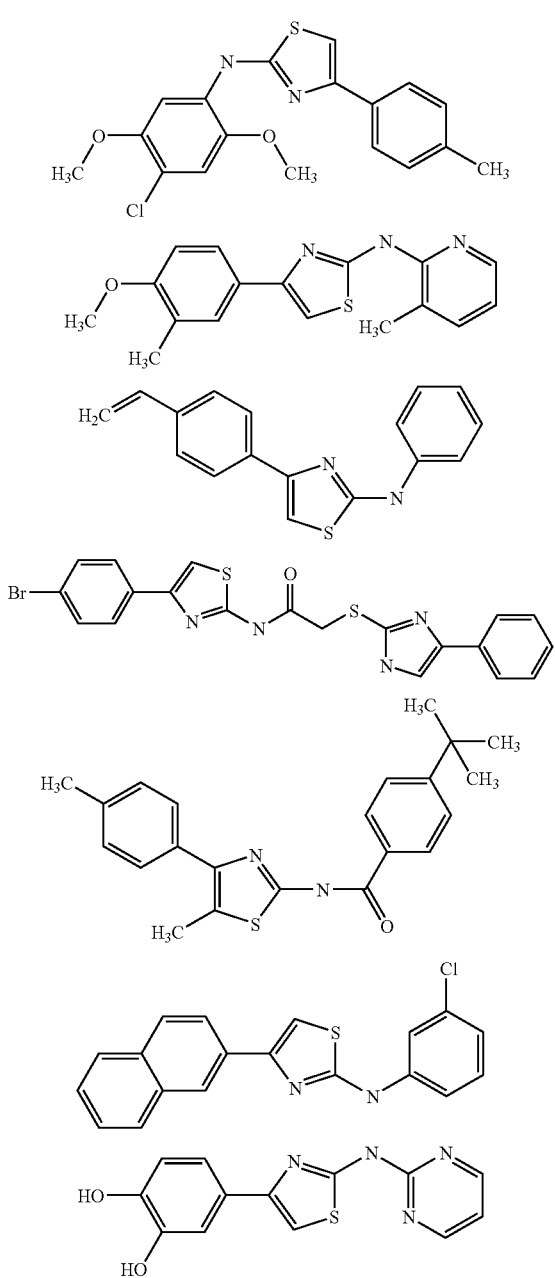

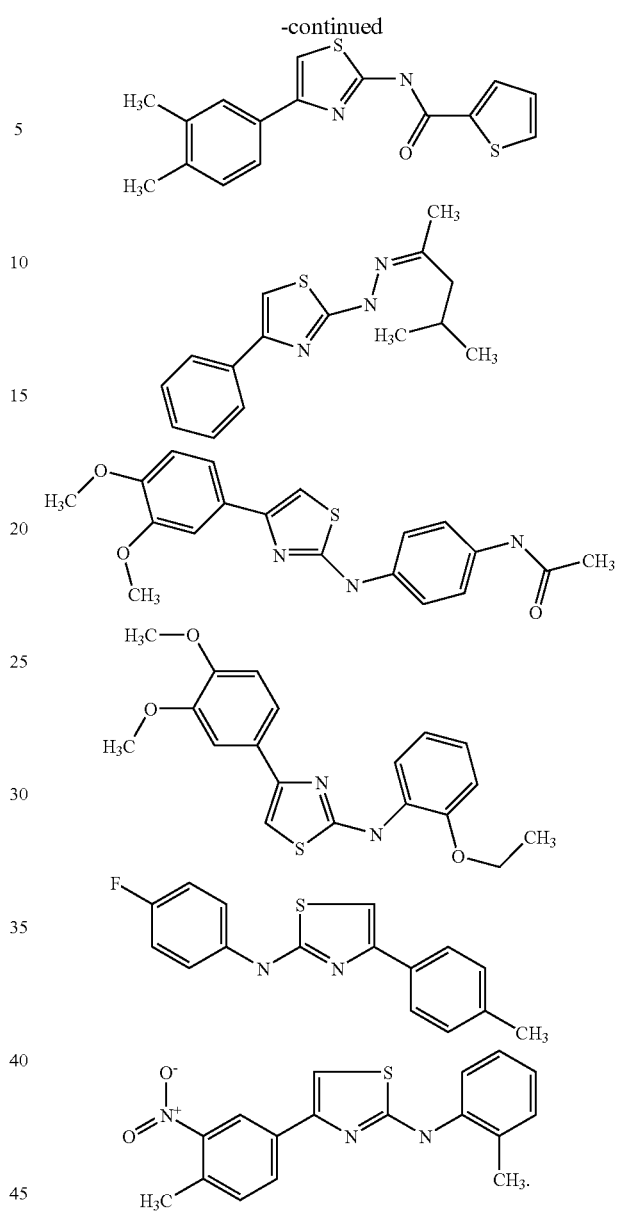

2-Quinazolinyl-4-Aminopyrimidinone Containing Compounds

In certain embodiments, the corrector compound of the present invention is a 2-Quinazolinyl-4-Aminopyrimidinone containing compounds described herein, which comprises a substituted or unsubstituted quinazoline group and a substituted or unsubstituted pyrimidine group. In specific embodiments, the subject compound are generally described by Formula (III) as follows:

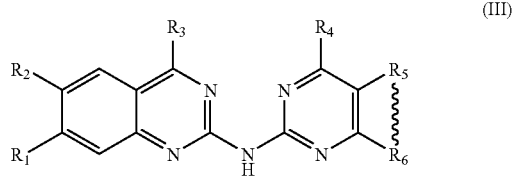

wherein $R_1$ and $R_2$ are independently selected from a hydrogen, an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, an alkoxy group, such as a methoxy group, ethoxy group, propoxy group; $R_3$ is an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $R_4$ is independently selected from a hydroxyl group or a carbonyl group; $R_5$ and $R_6$ are independently selected a fused cycloalkyl group, a hydrogen, an alkyl group such as a substituted or unsubstituted, a saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or a substituted or unsubstituted phenyl group, or a substituted or unsubstituted (heterocycloalkyl)alkyl group; or a pharmaceutically acceptable derivative thereof, as an individual stereoisomer or a mixture thereof. Exemplary substitutions for $R_1$, $R_2$, $R_3$, $R_4$, $R_5$, and $R_6$ are described in more detail below.

In certain embodiments, $R_1$ is independently chosen from a hydrogen, a lower allyl group (e.g., $C_1$-$C_4$), such as a methyl group or an ethyl group, or an alkoxy group, such as a methoxy group or an ethoxy group; $R_2$ is independently chosen from a hydrogen, a lower alkyl group (e.g., $C_1$-$C_4$), such as a methyl group or an ethyl group, or an alkoxy group, such as a methoxy group or an ethoxy group; $R_3$ is independently chosen from a lower alkyl group (e.g., $C_1$-$C_4$), such as a methyl group or an ethyl group; $R_4$ is independently selected from a hydroxyl group or a carbonyl group; and $R_5$ and $R_6$ are independently selected from a fused cycloalkyl group, such as a cyclopenyl group, a hydrogen, a lower alkyl group (e.g., $C_1$-$C_4$), such as a methyl group or an ethyl group, a substituted or unsubstituted phenyl group, a substituted or unsubstituted (heterocycloalkyl)alkyl group, such as a 2-methylthio-1H-benzoimidazole group.

In some embodiments of the invention, the 2-quinazolinyl-4-aminopyrimidinone containing compounds may comprise a formula of the following:

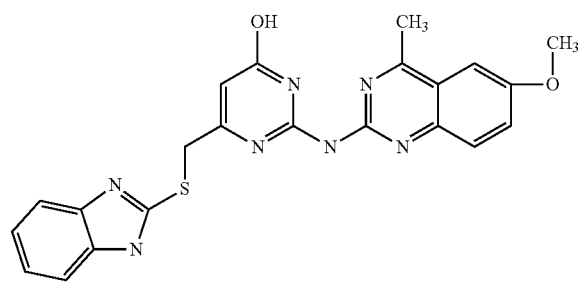

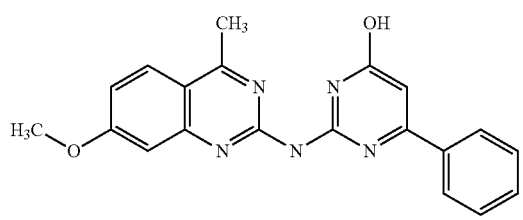

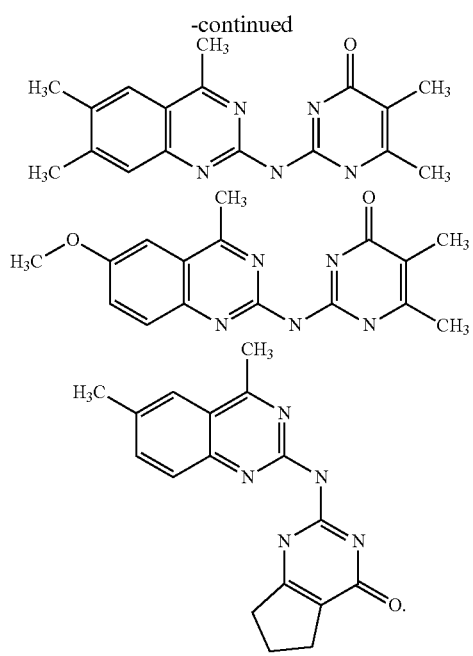

Bisaminomethylbithiazole Containing Compounds

In certain embodiments, the corrector compound of the present invention is a bisaminomethylbithiazole containing compounds described herein, which comprises a substituted bithiazole group and an unsubstituted heteroaromatic group. In specific embodiments, the subject compound are generally described by Formula (IV) as follows:

(IV)

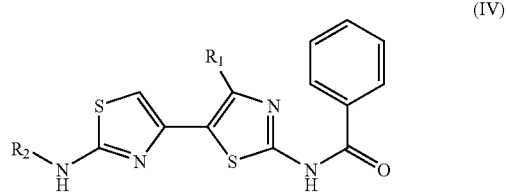

wherein $R_1$ is a alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; and $R_2$ is a substituted or unsubstituted phenyl group; or a pharmaceutically acceptable derivative thereof, as an individual stereoisomer or a mixture thereof. Exemplary substitutions for $R_1$ and $R_2$ are described in more detail below.

In certain embodiments, $R_1$ is a lower alkyl group (e.g., $C_1$-$C_4$), such as a methyl group; and $R_2$ is a mono- or di-substituted phenyl group having an alkoxy group, such as a methoxy group or an ethoxy group, a halogen, such as a chloride or a bromide, a nitro group, or a substituted or unsubstituted, saturated linear or branched hydrocarbon group or chain (e.g., $C_1$ to $C_8$) keto group, such as a ethanone group, a propanone group, a butanone group, or a pentanone group. In representative embodiments, $R_1$ is a methyl group, and $R_2$ is independently selected from a mono- or di-substituted phenyl group, such as a mono(nitro)phenyl group; a mono(alkoxy) phenyl, such as a 2-, 3-, 4-, or 5-methoxyphenyl, or a 2-, 3-, 4-, or 5-ethoxyphenyl, a mono(keto)phenyl, such as a 1-phenylpropan-1-one, or a 1-phenylethyl-1-one; or a di-substituted phenyl group, such as a 2-,3-,4-, or 5-(halo)-2-,3-,4-, or 5(alkoxy)phenyl, such as a 3-chloro-6-methoxyphenyl.

In some embodiments of the invention, the bisaminomethylbithiazole containing compounds may comprise a formula of the following:

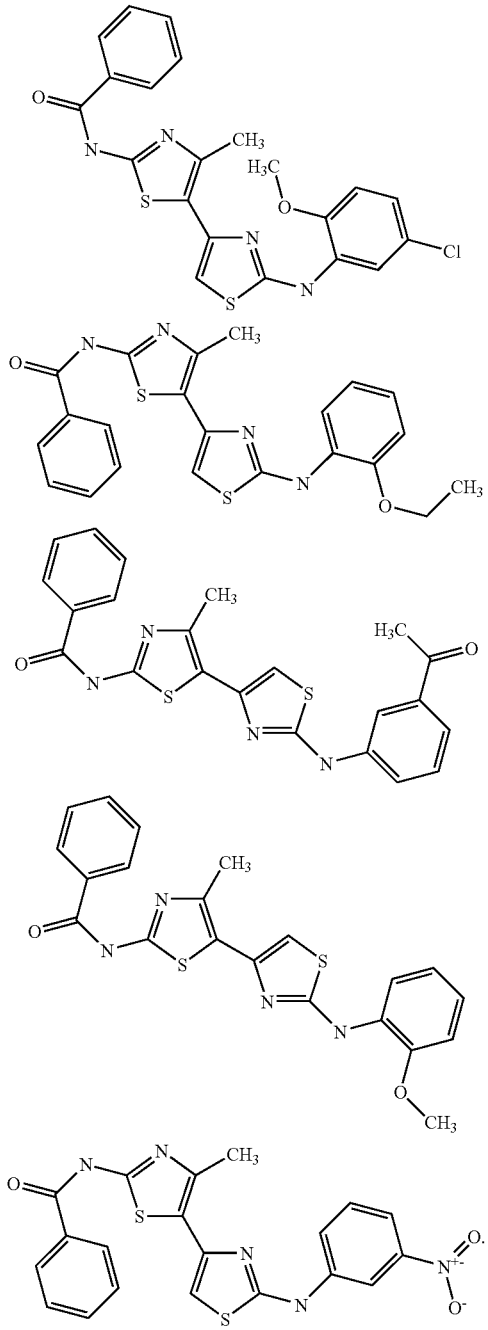

2-(N-phenylamino)quinoline Containing Compounds

In certain embodiments, the corrector compound of the present invention is a 2-(N-phenylamino)quinoline containing compounds described herein, which comprises a substituted or unsubstituted phenyl group and a substituted quinoline group. In specific embodiments, the subject compound are generally described by Formula (V) as follows:

(V)

$$\text{structure with } R_1, R_2, R_3, R_4, R_5$$

wherein $R_1$ is independently chosen from a hydrogen, or an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $R_2$ is independently chosen from a hydrogen, or an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $R_3$ is an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl; $R_4$ is independently chosen from a hydrogen, or an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or an alkoxy group, such as a methoxyl group or an ethoxyl group, or a halogen, such as bromine, chlorine, fluorine; and $R_5$ is independently chosen from a hydrogen, or an alkyl group such as a substituted or unsubstituted, saturated linear or branched hydrocarbon group or chain (e.g., $C_1$ to $C_8$) including, e.g., methyl, ethyl, isopropyl, tert-butyl, heptyl, n-octyl, dodecyl, octadecyl, amyl, 2-ethylhexyl, or an alkoxy group, such as a methoxyl group or an ethoxyl group, or a halogen, such as bromine, chlorine, fluorine; or a pharmaceutically acceptable derivative thereof, as an individual stereoisomer or a mixture thereof. Exemplary substitutions for $R_1$, $R_2$, $R_3$, $R_4$, and $R_5$ are described in more detail below.

In certain embodiments, $R_1$ is independently chosen from a hydrogen or an lower alkyl group (e.g., $C_1$-$C_4$), such as a methyl group; $R_2$ is independently a hydrogen or a lower alkyl group (e.g., $C_1$-$C_4$), such as a methyl group; $R_3$ is independently a hydrogen or a lower alkyl group (e.g., $C_1$-$C_4$), such as a methyl group; $R_4$ is independently chosen from a hydrogen, a halogen, such as bromine or chlorine, or an alkoxy group, such as a methoxyl group or an ethoxyl group; and $R_5$ is independently chosen from a hydrogen, a halogen, such as bromine or chlorine, or an alkoxy group, such as a methoxyl group or an ethoxyl group.

In some embodiments of the invention, the 2-(N-phenylamino)quinoline containing compounds may comprise a formula of the following:

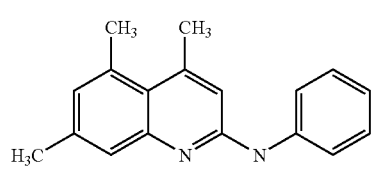

33
-continued

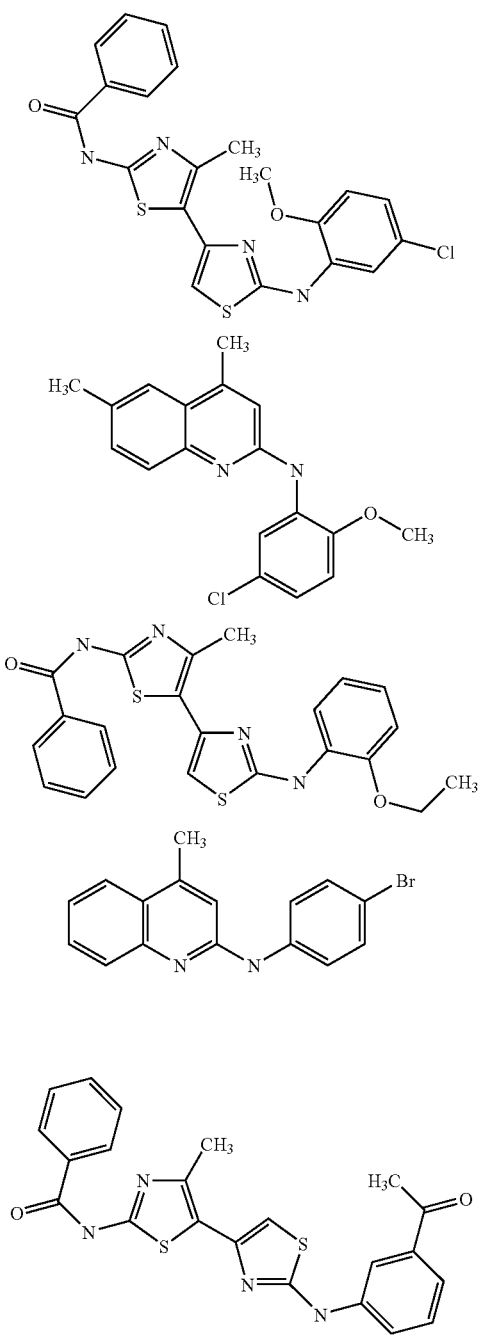

34
-continued

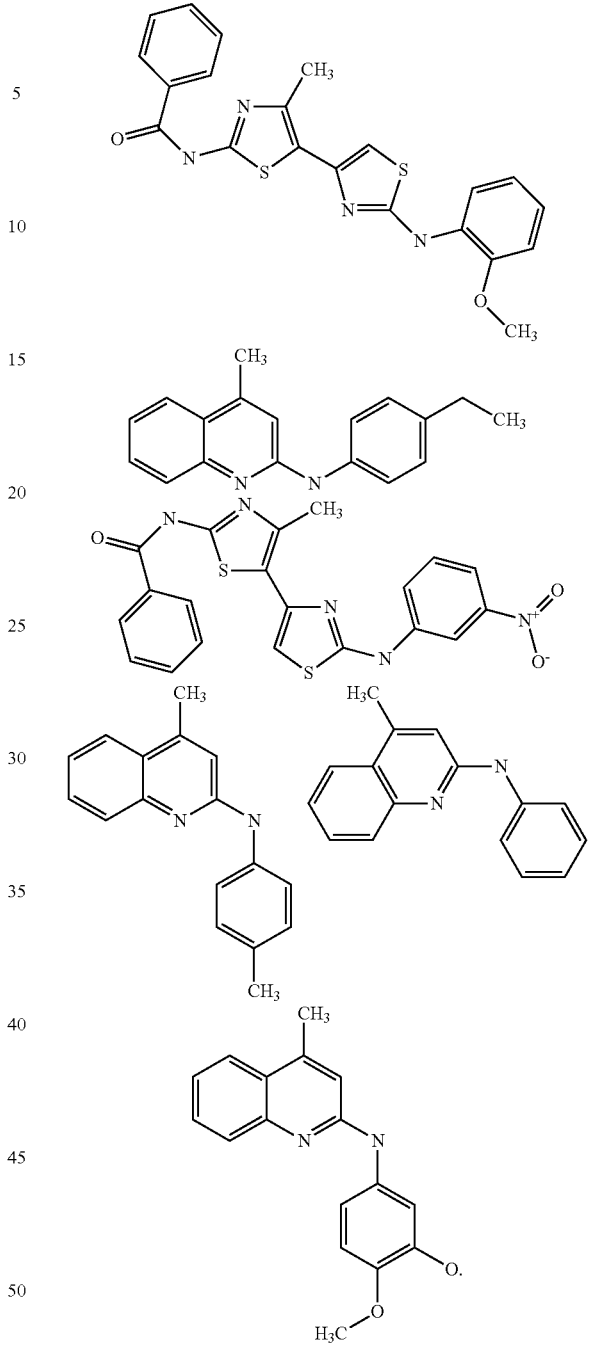

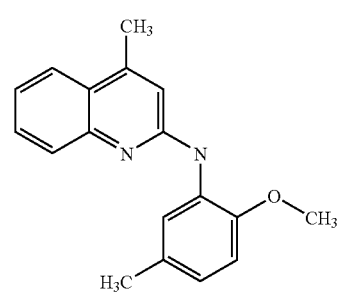

Analog and Derivative Compounds

Also provided by the invention are analogs and derivatives of the subject compounds described above. The terms "analog" and "derivative" refers to a molecule which is structurally similar or has the same function or activity as the subject compounds of the invention. Such analogs and derivatives of the subject compounds can be screened for efficiency in correcting folding or cellular processing of a mutant CFTR, such as ΔF508-CFTR.

In some embodiments, in silico modeling can be used to screen 3-dimensional libraries. of analog or derivative compounds for activity in binding to and correcting folding or cellular processing of a mutant CFTR, such as ΔF508-CFTR. An exemplary in silico modeling program suitable for use with the subject method is the PREDICT™ 3D Modeling Technology (Predix Pharmaceuticals, Woburn Mass.), described in greater detail in Becker et al., PNAS 101(31): 11304-11309 (2004).

Dosage Forms of Compounds of the Invention

In pharmaceutical dosage forms, the subject compounds of the invention may be administered in the form of their pharmaceutically acceptable salts, or they may also be used alone or in appropriate association, as well as in combination, with other pharmaceutically active compounds. The following methods and excipients are merely exemplary and are in no way limiting.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes, such as intrapulmonary or intranasal delivery.

Conventional and pharmaceutically acceptable routes of administration include intranasal, intrapulmonary intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

In one embodiment of particular interest, the compounds of the invention are administered in aerosol formulation via intrapulmonary inhalation. The compounds of the present invention can be formulated into pressurized acceptable propellants such as dichlorodifluoromethane, propane, nitrogen and the like.

Mechanical devices designed for intrapulmonary delivery of therapeutic products, include but are not limited to nebulizers, metered dose inhalers, and powder inhalers, all of which are familiar to those of skill in the art. Specific examples of commercially available devices suitable for the practice of this invention are the Ultravent nebulizer, manufactured by Mallinckrodt, Inc., St Louis, Mo.; the Acorn II nebulizer, manufactured by Marquest Medical Products, Englewood, Colo.; the Ventolin metered dose inhaler, manufactured by Glaxo Inc., Research Triangle Park, N.C.; the Spinhaler powder inhaler, manufactured by Fisons Corp., Bedford, Mass.; the "standing cloud" device of Inhale Therapeutic Systems, Inc., San Carlos, Calif.; the AIR inhaler manufactured by Alkennes, Cambridge, Mass.; and the AERx pulmonary drug delivery system manufactured by Aradigm Corporation, Hayward, Calif. Of particular interest are the PARI LC PLUS®, the PARI LC STAR®, and the PARI BABY™ nebulizers by PARI Respiratory Equipment, Inc., Monterey, Calif.

Formulations for use with a metered dose inhaler device may generally comprise a finely divided powder. This powder may be produced by lyophilizing and then milling a liquid conjugate formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations may then lyophilized and milled to the desired particle size.

The properly sized particles may then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants may include sorbitan trioleate and soya lecithin. Oleic acid may also be useful as a surfactant. This mixture may then loaded into the delivery device. An example of a commercially available metered dose inhaler suitable for use in the present invention is the Ventolin metered dose inhaler, manufactured by Glaxo Inc., Research Triangle Park, N.C.

Formulations for powder inhalers may comprise a finely divided dry powder containing conjugate and may also include a bulking agent, such as lactose, sorbitol, sucrose, or mannitol in amounts which facilitate dispersal of the powder from the device, e.g., 50% to 90% by weight of the formulation. The particles of the powder may have aerodynamic properties in the lung corresponding to particles with a density of about 1 g/cm.sup.2 having a median diameter less than 10 micrometers, preferably between 0.5 and 5 micrometers, most preferably of between 1.5 and 3.5 micrometers. An example of a powder inhaler suitable for use in accordance with the teachings herein is the Spinhaler powder inhaler, manufactured by Fisons Corp., Bedford, Mass. The powders for these devices may be generated and/or delivered by methods disclosed in U.S. Pat. Nos. 5,997,848, 5,993,783, 5,985, 248, 5,976,574, 5,922,354, 5,785,049 and 5,654,007.

For oral preparations, the subject compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver-their product continuously via electric pulses through unbroken skin for periods of several days or more.

The subject compounds of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agent can also be delivered to the subject by enteral administration. Enteral routes of administration include, but are not necessarily limited to, oral and rectal (e.g., using a suppository) delivery.

Furthermore, the subject compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Dosages of the Compounds of the Invention

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is one which provides up to about 1 µg to about 1,000 µg or about 10,000 µg of subject composition to reduce a symptom in a subject animal.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

Combination Therapy Using the Compounds of the Invention

For use in the subject methods, the subject compounds may be formulated with or otherwise administered in combination with other pharmaceutically active agents, including other mutant CFTR-activating agents or mutant-CFTR potentiating agents. The subject compounds may be used to provide an increase in the effectiveness of another chemical, such as a pharmaceutical (e.g., other CFTR-activating agents, or agents that potentiate a gating defective mutant-CFTR), or a decrease in the amount of another chemical, such as a pharmaceutical (e.g., other CFTR-activating agents), that is necessary to produce the desired biological effect.

Examples of other CFTR activating agents include, but are not limited to, enhancers of intracellular cAMP levels, such as for example, but not limited to, forskolin, rolipram, 8-bromo-cAMP, theophylline, papaverine, cAMP and salts, analogs, or derivatives thereof. Other examples include beta agonists, tobramycin (TOBI®, Chiron Inc., Emeryville, Calif.) and curcumin (Egan et al., (2004) Science 304:600-603). Examples of mutant-CFTR potentiating agents include, but are not limited to, phenylglycine containing compounds and sulfonamide containing compounds described in greater detail is U.S. Provisional Patent Application Ser. No. 60/576, 966, filed Jun. 4, 2004 incorporated herein in its entirety.

The compounds described above may also be combined with other therapies for CF, including oral corticosteroids, ibuprofen, ribovarin or antibiotics such as dicloxacillin, cephalosporin, cephalexin, erythromycin, amoxicillin-clavulanate, ampicillin, tetracycline, trimethoprim-sulfamethoxazole, chloramphenicol ciprofloxacin, tobramycin, gentamicin, cephalosporins, monobactams and the like.

The compounds described herein for use in combination therapy with the compounds of the present invention may be administered by the same route of administration (e.g. intrapulmonary, oral, enteral, etc.) that the compounds are administered. In the alternative, the compounds for use in combination therapy with the compounds of the present invention may be administered by a different route of administration that the compounds are administered.

Kits

Kits with unit doses of the subject compounds, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Methods

Methods for Increasing Chloride Ion Permeability of a Mutant-CFTR Cell

The invention provides methods for increasing ion permeability of a cell that produces mutant-CFTR protein, with cells having a folding or processing defective mutant-CFTR being of interest, such as cells having a ΔF508-CFTR being of particular interest. In general, the method involves contacting the cell with a compound in an amount effective to correct the folding or processing defect of a mutant-CFTR protein and increase ion permeability of the cell. In one embodiment of particular interest, a compound of the invention is used in the method in combination with a second mutant-CFTR activator or potentiator.

In many embodiments, the cell mutant-CFTR protein is present on the plasma membrane of the cell. Methods of detecting mutant-CFTR protein presence on the plasma membrane are well known in the art and can include but are not limited to, for example, labeling a molecule that binds to CFTR protein with a fluorescent, chemical or biological tag. Examples of molecules that bind to CFTR protein include, without limitation, antibodies (monoclonal and polyclonal), FAB fragments, humanized antibodies and chimeric antibodies. For an example of an antibody that binds to CFTR protein, see, e.g. U.S. Pat. No. 6,201,107.

In many embodiments, the cell has increased permeability to chloride ions, and the contacting of the cell with a compound of the invention, particularly when provided in combination with a mutant-CFTR activator or potentiator, increases the rate of chloride ion transport across the plasma membrane of the cell. Contacting the cell with a compound of the invention usually increases the activity of mutant-CFTR protein to increase ion transport.

In most embodiments, the ion transport activity of mutant-CFTR, or the permeability of a cell to ions, is increased by up to about 10%, by up to about 20%, by up to about 50%, by up to about 100%, by up to about 150%, by up to about 200%, by up to about 300%, by up to about 400%, by up to about 500%, by up to about 800%, or up to about 1000% or more. In certain embodiments, where there is no detectable ion transport activity of mutant-CFTR or permeability of a cell to ions, contacting of the cell with a compound of the invention causes detectable activity of mutant-CFTR or permeability of a cell to ions.

Activation of mutant-CFTR and/or ion permeability may be measured using any convenient methods that may use molecular markers, e.g., a halide sensitive GFP or another molecular marker (e.g., Galietta et al., (2001) FEBS Lett. 499, 220-224), patch clamp assays, and short circuit assays.

Suitable cells include those cells that have an endogenous or introduced mutant-CFTR gene. Suitable cells include mammalian cell systems (e.g., COS, CHO, BHK, 293, 3T3 cells etc.) harboring constructs that have an expression cassette for expression of mutant-CFTR; The cell used in the subject methods may be a cell present in vivo, ex vivo, or in vitro. As used herein, the term "expression cassette" is meant to denote a genetic sequence, e.g. DNA or RNA, that codes for mutant-CFTR protein, e.g., ΔF508-CFTR. Methods of introducing an expression cassette into a cell are well known in the art, see for example, Sambrook et al., *Molecular Cloning: A Laboratory Manual*. Cold Spring Harbor Laboratory Press, NY, Vol. 1, 2, 3 (1989).

Methods of Treating Cystic Fibrosis

The invention also provides methods of treating a subject having a condition associated with mutant-CFTR, e.g., cystic fibrosis. In general, the method involves administering to the subject a compound of the invention in an amount effective to activate a mutant-CFTR protein to increase ion transport and thereby treat the condition. In an embodiment of particular interest, a compound of the invention is administered in combination with a second mutant-CFTR activator or potentiator, e.g., a compound that enhances intracellular cAMP, e.g., forskolin, a phenylglycine containing compound, or a sulfonamide containing compound.

The compounds disclosed herein are useful in the treatment of a mutant-CFTR-mediated condition, e.g., any condition, disorder or disease, or symptom of such condition, disorder, or disease, that results from the presence and/or activity of mutant-CFTR as compared to wild-type CFTR, e.g., activity of mutant-CFTR in ion transport. Such conditions, disorders, diseases, or symptoms thereof are amenable to treatment by correction of folding or cellular processing of mutant-CFTR, e.g., activation of mutant-CFTR chloride transport. Cystic fibrosis, a hereditary condition associated with a mutant-CFTR, e.g., ΔF508-CFTR is an example of a condition that is treatable using the compounds of the invention. Use of the compounds of the invention in combination with a second mutant CFTR activator or potentiator is of particular interest.

Cystic fibrosis is predominantly a disorder of infants, children and young adults, in which there is widespread dysfunction of the exocrine glands, characterized by signs of chronic pulmonary disease (due to excess mucus production in the respiratory tract), pancreatic deficiency, abnormally high levels of electrolytes in the sweat and occasionally by biliary cirrhosis. Also associated with the disorder is an ineffective immunologic defense against bacteria in the lungs.

Pathologically, the pancreas shows obstruction of the pancreatic ducts by amorphous eosinophilic concretions, with consequent deficiency of pancreatic enzymes, resulting in steatorrhoea and azotorrhoea and intestinal malabsorption.

The degree of involvement of organs and glandular systems may vary greatly, with consequent variations in the clinical picture.

Nearly all exocrine glands are affected in cystic fibroses in varying distribution and degree of severity. Involved glands are of three types: those that become obstructed by viscid or solid eosinophilic material in the lumen (pancreas, intestinal glands, intrahepatic bile ducts, gallbladder, submaxillary glands); those that are histologically abnormal and produce an excess of secretions (tracheobronchial and Brunner's glands); and those that are histologically normal but secrete excessive sodium and chloride (sweat, parotid, and small salivary glands). Duodenal secretions are viscid and contain an abnormal mucopolysaccharide. Infertility occurs in 98% of adult men secondary to maldevelopment of the vas deferens or to other forms of obstructive azoospermia. In women, fertility is decreased secondary to viscid cervical secretions, but many women with CF have carried pregnancies to term. However, the incidence of maternal complications increases.

Fifty percent of cystic fibrosis patients with pulmonary manifestations usually chronic cough and wheezing associated with recurrent or chronic pulmonary infections. Cough is the most troublesome complaint, often accompanied by sputum, gagging, vomiting, and disturbed sleep. Intercostal retractions, use of accessory muscles of respiration, a barrel-chest deformity, digital clubbing, and cyanosis occur with disease progression. Upper respiratory tract involvement includes nasal polyposis and chronic or recurrent sinusitis. Adolescents may have retarded growth, delayed onset of puberty, and a declining tolerance for exercise. Pulmonary complications in adolescents and adults include pneumothorax, hemoptysis, and right heart failure secondary to pulmonary hypertension.

Pancreatic insufficiency is clinically apparent in 85 to 90% of CF patients, usually presents early in life, and may be progressive. Manifestations include the frequent passage of bulky, foul-smelling, oily stools; abdominal protuberance; and poor growth pattern with decreased subcutaneous tissue and muscle mass despite a normal or voracious appetite. Rectal prolapse occurs in 20% of untreated infants and toddlers. Clinical manifestations may be related to deficiency of fat-soluble vitamins.

Excessive sweating in hot weather or with fever may lead to episodes of hypotonic dehydration and circulatory failure. In arid climates, infants may present with chronic metabolic alkalosis. Salt crystal formation and a salty taste on the skin are highly suggestive of CF.

Insulin-dependent diabetes develops in 10% of adult patients having CF, and multilobular biliary cirrhosis with varices and portal hypertension develops in 4 to 5% of adolescents and adults. Chronic and/or recurrent abdominal pain may be related to intussusception, peptic ulcer disease, periappendiceal abscess, pancreatitis, gastroesophageal reflux, esophagitis, gallbladder disease, or episodes of partial intestinal obstruction secondary to abnormally viscid fecal contents. Inflammatory complications may include vasculitis and arthritis.

Any of above symptoms of CF may be treated using the compounds of the invention, with use of such compounds in combination with a second mutant-CFTR activator or potentiator being of particular interest.

The above methods may be used to treat CF and its symptoms in humans or in animals. Several animal models for CF are known in the art. For example, Engelhardt et al. (*J. Clin. Invest.* 90: 2598-2607, 1992) developed an animal model of the human airway, using bronchial xenografts engrafted on rat tracheas and implanted into nude mice. More recently transgenic models of cystic fibrosis have been produced (e.g., Clarke et al., *Science* 257: 1125-1128, 1992; Dorin et al., *Nature* 359: 211-215, 1992). With the recent advances of nuclear transfer and stem cell transformation technologies, the alteration of a wild type CFTR gene in an animal to make it into a mutant-CFTR gene is possible for a wide variety of animals.

Many of these animals show human CF symptoms. In particular, many of these animals showed measurable defects in ion permeability of airway and intestinal epithelia, similar to those demonstrable in human CF tissues, and a susceptibility to bacterial infection. Furthermore, most of the deficient mice had intestinal pathology similar to that of meconium ileus. Also, there appeared to be no prenatal loss from litters produced from crosses between heterozygotes.

Animals suitable for treatment using the subject methods include any animal with a mutant-CFTR related condition, particularly a mammal, e.g., non-human primates (e.g., monkey, chimpanzee, gorilla, and the like), rodents (e.g., rats, mice, gerbils, hamsters, ferrets, and the like), lagomorphs, swine (e.g., pig, miniature pig), equine, canine, feline, and the like. Large animals are of particular interest. Transgenic mammals may also be used, e.g. mammals that have a chimeric gene sequence. Methods of making transgenic animals are well known in the art, see, for example, U.S. Pat. No. 5,614,396. For an example of a transgenic mouse with a CFTR defect, see e.g. WO 94/04669.

Such animals may be tested in order to assay the activity and efficacy of the subject compounds. Improvement in lung function can be assessed by, for example, monitoring prior to and during therapy the subject's forced vital capacity (FVC), carbon monoxide diffusing capacity ($DL_{CO}$), and/or room air $pO_2 > 55$ mmHg at rest. Significant improvements in one or more of these parameters are indicative of efficacy. It is well within the skill of the ordinary healthcare worker (e.g., clinician) provide adjust dosage regimen and dose amounts to provide for optimal benefit to the patient according to a variety of factors (e.g., patient-dependent factors such as the severity of the disease and the like), the compound administered, and the like).

Subjects Suitable for Treatment

Subjects suitable for treatment with a method of the present invention include individuals having mutant-CFTR protein-mediated condition disorder or disease, or symptom of such condition, disorder, or disease that results from or is correlated to the presence of a mutant-CFTR, usually two alleles of the mutant CFTR. Moreover, subjects suitable for treatment with a method of the present invention include individuals with Cystic Fibrosis (CF). Of particular interest in many embodiments is the treatment of humans with CF.

Symptoms of mutant-CFTR protein-mediated conditions include meconium ileus, liver disease including biliary tract obstruction and stenosis, pancreatic insufficiency, pulmonary disease including chronic *Pseudomonas aeruginosa* infections and other infections of the lung, infertility associated with abnormal vas deferens development or abnormal cervical mucus, and carcinoma including adenocarcinoma.

The compounds of the present invention affect the ion transport capability of the mutant-CFTR by increasing the reduced level of ion transport mediated by a mutant-CFTR, such as the ΔF508-CFTR. As such, the compounds of the present invention have particular clinical utility in treating a subset of CF patients that have mutations in the CFTR gene that results a mutant-CFTR that is expressed in the plasma membrane and has reduced chloride conductance capability due to folding or cellular processing defects (i.e., the mutant-CFTR is folding or cellular processing defective). As such, the compounds of the present invention have clinical utility in treating CF patients having a folding or cellular processing mutant-CFTR, such as ΔF508-CFTR. In addition, the compounds of the present invention also have clinical utility in treating CF patients when used in conjunction with compounds that activate or potentiate a gating defective mutant-CFTR, such as ΔF508-CFTR, G551D-CFTR, G1349D-CFTR, or D1152H-CFTR.

CFTR mutations associated with CF are well known in the art. These mutations can be classified in five general categories with respect to the CFTR protein. These classes of CFTR dysfunction include limitations in CFTR production (e.g., transcription and/or translation) (Class I), aberrant folding and/or trafficking (Class II), abnormal regulation of conduction (Class III), decreases in chloride conduction (Class IV), and reductions in synthesis (Class V). Due to the lack of functional CFTR, Class I, II, and III mutations are typically associated with a more severe phenotype in CF (i.e. pancreatic insufficiency) than the Class IV or V mutations, which may have very low levels of functional CFTR expression. A listing of the different mutations that have been identified in the CFTR gene is as found at the world-wide website of the Cystic Fibrosis Mutation Database at genet.sickkids.on.ca/cgi-bin/WebObjects/MUTATION, specifically incorporated by reference herein in its entirety.

A subject suitable for treatment with a method of the present invention may be homozygous for a specific mutant-CFTR, i.e. homozygous subjects with two copies of a specific mutant-CFTR, e.g., ΔF508-CFTR. In addition, subjects suitable for treatment with a method of the present invention may also be compound heterozygous for two different CFTR mutants, i.e., wherein the genome of the subjects includes two different mutant forms of CFTR, e.g., a subject with one copy of ΔF508-CFTR and a copy of different mutant form of CFTR.

In some embodiments of the invention, the mutant-CFTR polypeptide is ΔF508-CFTR. The invention, however, should not be construed to be limited solely to the treatment of CF patients having this mutant form of CFTR. Rather, the invention should be construed to include the treatment of CF patients having other mutant forms of CFTR with similar characteristics, that result in expression of the mutant-CFTR in the plasma membrane and has reduced chloride conductance capability or has abnormal regulation of conductance.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials are used in the examples below.

Cell Lines

Fischer rat thyroid (FRT) epithelial cells stably co-expressing human ΔF508-CFTR and the high-sensitivity halide-sensing green fluorescent analog YFP-H148Q/I152L (Galietta et al., FEBS Lett 499:220-224 (2001)) were generated as described previously (Galietta et al., JBC 276:19723-19728 (2001); Ma et al., JBC 277:37235-37241 (2002)). FRT cells stably expressing P574H-CFTR were generated similarly. FRT cells were cultured on plastic in Coon's modified F12 medium supplemented with 10% fetal bovine serum, 2 mM L-glutamine, 100 U/ml penicillin, and 100 µg/ml streptomycin. For primary screening, cells were plated using a LabSystems multidrop dispenser into black 96-well microplates (Corning-Costar) at 50,000 cells/well. Screening was done at 18-24 hours after plating. For short-circuit current measurements cells were cultured on Snapwell permeable supports (Corning-Costar) at 500,000 cells/insert. Human nasal epithelial cells from ΔF508/ΔF508 homozygous CF subjects (or an N1303K/N1303K homozygous subject) were cultured on Snapwell inserts and allowed to differentiate in a hormone-supplemented medium as described (Galietta et al., Am. J. Physiol. 275:L917-L923 (1998)).

Compounds

A collection of 150,000 diverse drug-like compounds (>90% with molecular size 250-500 daltons, ChemDiv and ChemBridge, San Diego, Calif.) was used for initial screening. For optimization, >1500 commercially-available analogs of active compounds identified in the primary screen were tested. Plates containing one or four compounds per well were prepared for screening (1 mM in DMSO). Compounds for secondary analysis were confirmed by NMR and liquid chromatography/mass spectrometry.

Screening Procedures

Screening was carried out using a Beckman integrated system containing a 3-meter robotic arm, $CO_2$ incubator containing microplate carousel, plate-washer, liquid handling workstation, bar code reader, delidding station, plate sealer, and two FluoStar fluorescence plate readers (Optima, BMG Lab Technologies), each equipped with dual syringe pumps and 500±10 nm excitation and 535±15 nm emission filters (Chroma). FRT cells were incubated at 37° C. (90% humidity, 5% $CO_2$) for 18-24 hours, and then incubated for 18-24 hours 50 µL of medium containing test compounds (10 µM final concentrations). At the time of the assay cells were washed with PBS and then incubated with PBS containing forskolin (20 µM) and genistein (50 µM). Each well was assayed individually for $I^-$ influx in a plate reader by recording fluorescence continuously (200 ms per point) for 2 seconds (baseline) and then for 12 seconds after rapid (<1 second) addition of 165 µL of PBS in which 137 mM $Cl^-$ was replaced by $I^-$. $I^-$ influx rate was computed by fitting the final 11.5 second of the data to an exponential for extrapolation of initial slope, and normalizing for background-subtracted initial fluorescence. All compound plates contained negative controls (DMSO vehicle) and positive controls (4-PBA, 4 mM), with separate low temperature rescue (27° C. incubation for 18-24 hours) positive control plates. Assay analysis indicated a Z'-factor of >0.6.

Transepithelial Current Measurements

ΔF508-CFTR expressing FRT cells were cultured on Snapwell inserts for 7-9 days. Test compounds were added 18-24 hours prior to measurements. The basolateral solution contained (in mM): 130 NaCl, 2.7 KCl, 1.5 $KH_2PO_4$, 1 $CaCl_2$, 0.5 $MgCl_2$, 10 glucose, 10 Na-Hepes (pH 7.3). In the apical bathing solution 65 mM NaCl was replaced by Na gluconate, and $CaCl_2$ was increased to 2 mM. Solutions were bubbled with air and maintained at 37° C. The basolateral membrane was permeabilized with 250 µg/ml amphotericin B. For human bronchial epithelial cells, apical and basolateral chambers contained 126 mM NaCl, 0.38 mM $KH_2PO_4$, 2.1 mM $K_2HPO_4$, 1 mM $MgSO_4$, 1 mM $CaCl_2$, 24 nM $NaHCO_3$ and 10 mM glucose (basolateral membrane not permeabilized). Hemichambers were connected to a DVC-1000 voltage clamp (World Precision Instruments) via Ag/AgCl electrodes and 1 M KCl agar bridges for recording apical membrane or short-circuit current.

Analysis of Corrector Mechanisms

Biochemical studies utilized BHK cells stably transfected with HA-tagged variants of wildtype and ΔF508-CFTR. CFTR was tagged at the C-terminal tail (CFTR-$C_t$HA) or in its fourth extracellular loop with three HA epitopes (CFTR-3HA). Accumulation of complex-glycosylated CFTR was assayed by immunoblot analysis as described (Sharma et al., JBC 276:8942-8950 (2001)). Plasma membrane expression was assayed by HA antibody binding (in non-permeabilized cells) using an iodinated secondary anti-mouse antibody as described (Sharma et al., JCB 164:923-933 (2004)) or a horseradish peroxidase-coupled secondary antibody with Amplex-red as substrate. Non-specific antibody binding was measured in non-transfected cells (using same assay conditions) and in transfected cells with primary antibody omitted. Folding efficiency was assayed as described (Du et al., Nat. Struct. Mo. Biol. (2005)) with modifications. ΔF508-CFTR-$C_t$HA expressing BHK cells were depleted of endogenous methionine and cysteine in the presence of correctors. To monitor folding, cells were incubated in the presence of 0.2 mCi/ml $^{35}$S-methionine and $^{35}$S-cysteine for 150 minutes and chased in the presence of complete culture medium for an additional 150 minutes. Radioactivity incorporated into newly synthesized CFTR was measured by pulse-labeling equal numbers of cells for 15 minutes without chase. CFTR was isolated by immunoprecipitation, visualized by fluorography, and quantified by phosphorimage analysis as described (Lukacs et al, EMBO J., 13:6076-6086 (1994)).

Example 1

Discovery and Characterization of ΔF508-CFTR Correctors

Figure 2:
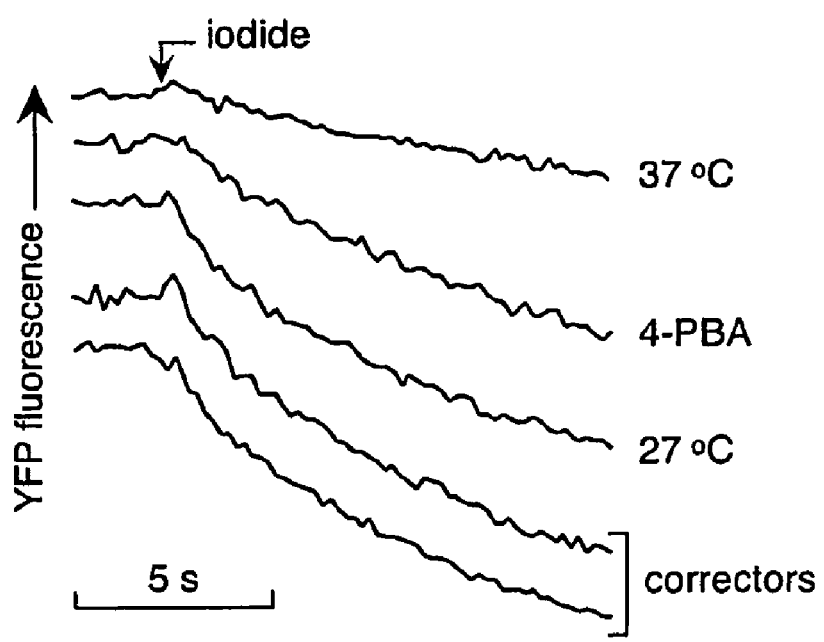
FIG. 2 shows representative traces showing iodide influx under control conditions (37° C.) or after 24 hour incubation at 27° C. or with 4-PBA (4 mM), or corrector compounds (10 μM, 37° C.).

As depicted in FIG. 1, FRT cells coexpressing ΔF508-CFTR and a fluorescent YFP halide sensor were incubated with test compounds (10 µM) for 18-24 hours at 37° C. in a 96-well format. ΔF508-CFTR mediated iodide influx was then assayed after compound washout and addition of the potentiators forskolin and genistein. Primary screening of 150,000 compounds produced 45 compounds that increased iodide influx (Δd[T]/dt) by >0.10 µmM/s, and 15 compounds increasing iodide influx by >0.20 mM/s. Examples of original data from individual wells are shown in FIG. 2. The negative control was vehicle (DMSO) alone (labelled '37° C.'), and the positive controls were 4-phenylbutyrate (4-PBA) and reduced temperature (27° C.) incubation rescue. Examples of two active compounds are shown.

Figure 3:
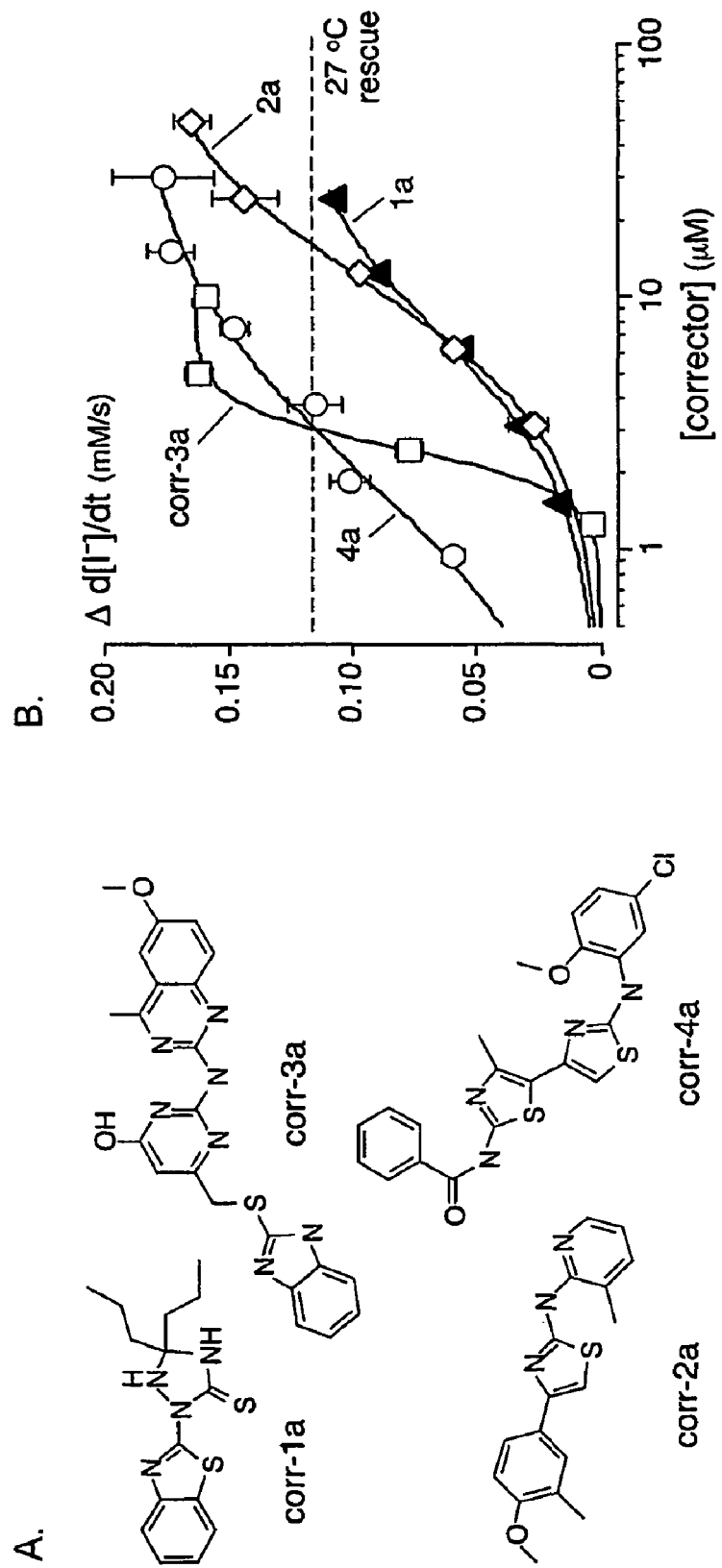
FIG. 3 shows chemical structures of representative corrector compounds in Panel A, and dose-response data for the indicated corrector compounds (SE, n=5) in Panel B.
Figure 4:
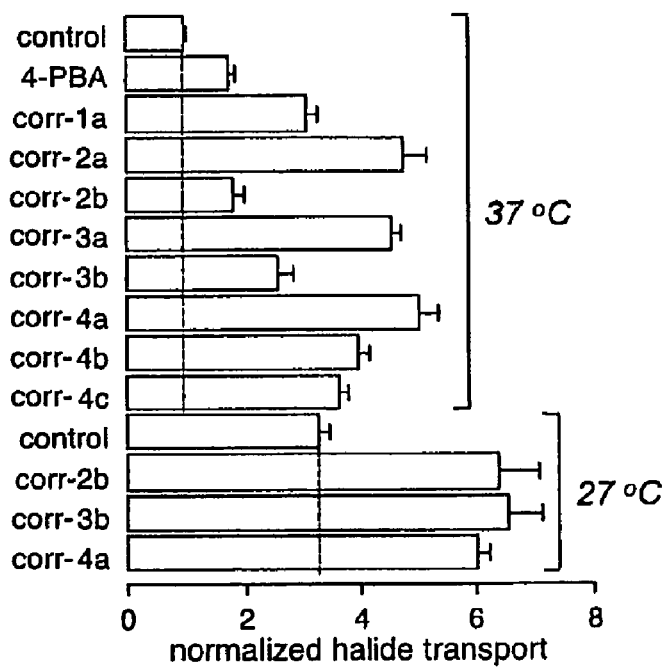
FIG. 4 is a graph summarizing the maximal iodide influx (normalized to 37° C. control) in ΔF508-CFTR expressing FRT cells incubated at 37° C. or 27° C. (SE, n=5) with the indicated corrector compound. Iodide influx increased significantly ($p<0.01$) for all compounds compared to control cells.

Active compounds were retested, and ΔF508-CFTR specificity was verified by inhibition of the increased iodide influx by $CFTR_{inh}$-172, and lack of corrector effect on FRT null cells. Initial optimization of corrector compound activity was done by screening of commercially-available analogs. Three rounds of optimization with testing of >1500 compounds of five chemical scaffolds gave active correctors of the aminobenzothiazole, aminoarylthiazole, quinazolinylaminopyrimidinone, bisaminomethylbithiazole and phenylaminoquinoline chemical classes, four of which are shown in FIG. 3, panel A. Dose-response data are shown in FIG. 3, panel B, referenced against 27° C. rescue shown as the dashed line. A listing of 37 correctors and their potencies ($K_a$, $V_{max}$) is provided in Table 1, which establishes a structure-activity data set for the five corrector classes. FIG. 4 summarizes $V_{max}$ data for several correctors, comparing to positive and negative controls. Several compounds gave greater $V_{max}$ than 27° C. rescue, and compounds were found to have additive effect on iodide influx when combined with 27° C. rescue.

Figure 5:
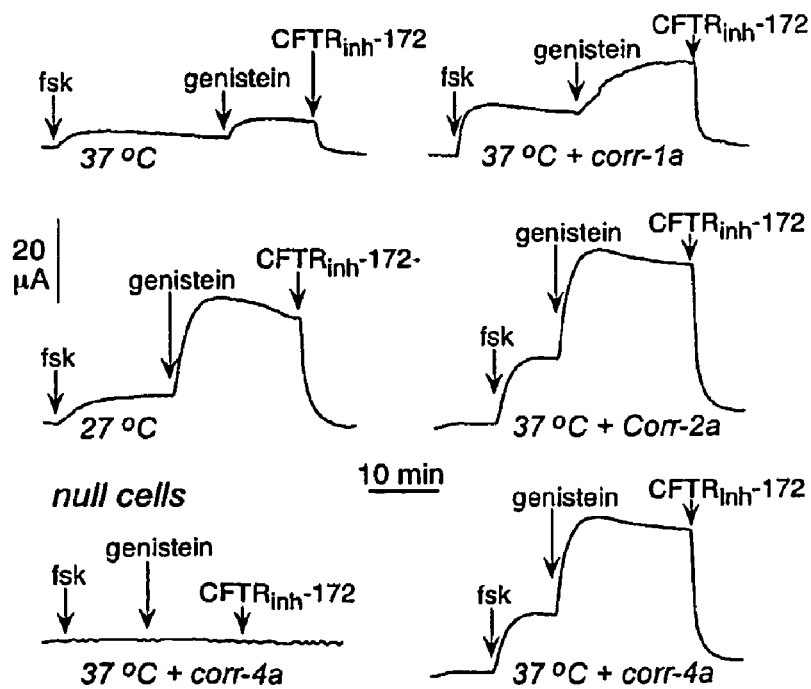
FIG. 5 shows apical membrane chloride current measurements in Ussing chambers after basolateral membrane permeabilization and in the presence of a chloride gradient. Concentrations: forskolin (20 μM), genistein (50 μM), $CFTR_{inh}$-172 (10 μM). Lower left, measurements done on FRT null cells (other panels ΔF508-CFTR expressing FRT cells).

FIG. 5 shows Ussing chamber experiments in which apical membrane chloride current was measured in FRT cells after basolateral membrane permeabilization and in the presence of a chloride gradient (apical 65 mM, basolateral 130 mM). After measurement of apical membrane chloride current at baseline, high concentrations of the potentiators forskolin (20 μM) and then genistein (50 μM) were added; CFTR$_{inh}$-172 (10 μM) was added at the end of each experiment. The electrophysiological studies confirmed the data obtained from the fluorescence assay. In the left panel in FIG. 5 is shown the much greater current in ΔF508-CFTR expressing cells grown at 27° C. vs. 37° C. (top and middle curves), and the lack of corrector effect on FRT null cells (bottom). Incubation with correctors at 37° C. in ΔF508-CFTR expressing cells for 24 hours prior to measurements produced increased forskolin/genistein stimulated and CFTR$_{inh}$-172 inhibited chloride currents (FIG. 5, right panel), comparable to or greater than that produced by 27° C. rescue.

TABLE 1

| | | $V_{max}$ (mM/s) | $K_a$(μM) |
|---|---|---|---|
| Class 1: 2-aminobenzothiazoles | | | |
| corr-1a | [structure] | 0.11 ± 0.01 | 7.4 ± 0.9 |
| corr-1b | [structure] | 0.11 ± 0.01 | 16.5 ± 0.9 |
| corr-1c | [structure] | 0.07 ± 0.01 | 2.5 ± 0.3 |
| corr-1d | [structure] | 0.08 ± 0.01 | 5.9 ± 0.8 |
| corr-1e | [structure] | 0.08 ± 0.01 | 9.0 ± 0.2 |
| corr-1f | [structure] | 0.17 ± 0.01 | 8.0 ± 1.0 |

TABLE 1-continued

|  |  | $V_{max}$ (mM/s) | $K_a$ (μM) |
|---|---|---|---|
| Class 2: 2-amino-4-arylthiazoles | | | |
| corr-2a | | 0.22 ± 0.01 | 12.1 ± 0.4 |
| corr-2b | | 0.21 ± 0.02 | 16 ± 0.3 |
| corr-2c | | 0.10 ± 0.02 | 16.4 ± 0.8 |
| corr-2d | | 0.10 ± 0.02 | 8.2 ± 0.6 |
| corr-2e | | 0.10 ± 0.01 | 6.3 ± 0.8 |
| corr-2f | | 0.15 ± 0.01 | 7.3 ± 0.5 |
| corr-2g | | 0.15 ± 0.01 | 8.1 ± 0.1 |
| corr-2h | | 0.10 ± 0.01 | 9.1 ± 0.7 |

TABLE 1-continued
| | | $V_{max}$ (mM/s) | $K_a$ (μM) |
|---|---|---|---|
| corr-2i | 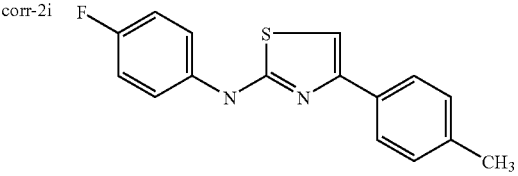 | 0.09 ± 0.01 | 5.5 ± 0.1 |
| corr-2j | 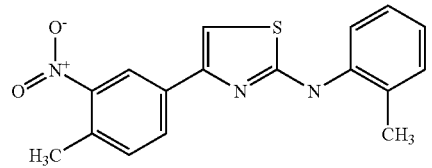 | 0.10 ± 0.01 | 15 ± 2 |
| corr-2k | 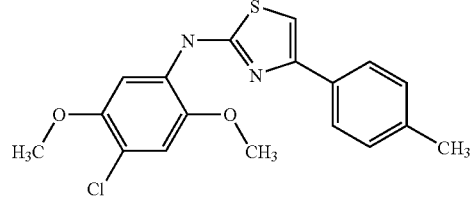 | 0.15 ± 0.01 | 10.2 ± 0.2 |
| corr-2l | 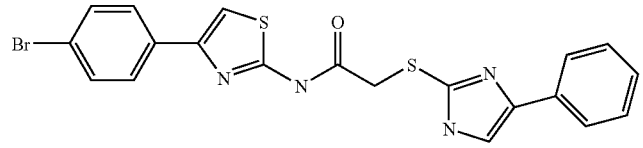 | 0.15 ± 0.01 | 11.3 ± 0.2 |
| corr-2m | 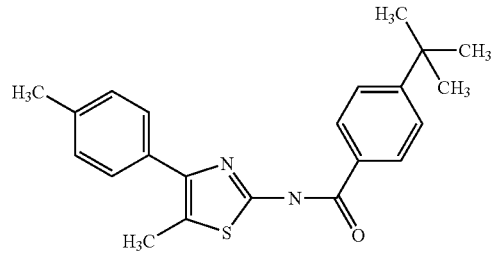 | 0.11 ± 0.01 | 14.9 ± 0.9 |
Class 3: 2-quinazolinyl-4-aminopyrimidinones
| | | | |
|---|---|---|---|
| corr-3a | 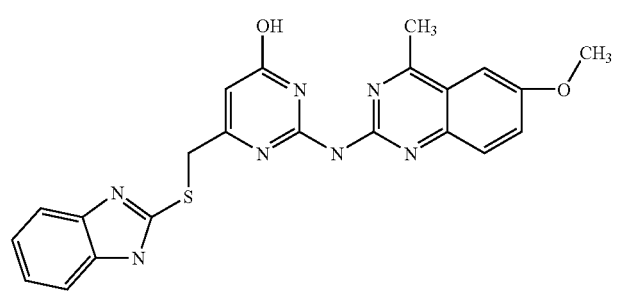 | 0.13 ± 0.01 | 2.6 ± 0.1 |
| corr-3b | 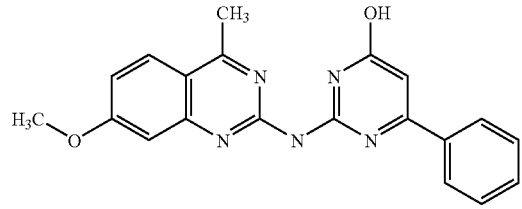 | 0.17 ± 0.02 | 11.8 ± 0.6 |

TABLE 1-continued

| | | $V_{max}$ (mM/s) | $K_a$ (μM) |
|---|---|---|---|
| corr-3c | [structure] | 0.15 ± 0.01 | 8.8 ± 0.3 |
| corr-3d | [structure] | 0.20 ± 0.07 | 15.2 ± 0.4 |
| corr-3e | [structure] | 0.19 ± 0.01 | 13.9 ± 0.5 |

Class 4: bisaminomethylbithiazoles

| | | $V_{max}$ (mM/s) | $K_a$ (μM) |
|---|---|---|---|
| corr-4a | [structure] | 0.21 ± 0.02 | 2.8 ± 0.1 |
| corr-4b | [structure] | 0.20 ± 0.01 | 5.3 ± 0.1 |
| corr-4c | [structure] | 0.16 ± 0.01 | 1.7 ± 0.1 |

TABLE 1-continued

| | | $V_{max}$ (mM/s) | $K_a$ (μM) |
|---|---|---|---|
| corr-4d | (structure) | 0.21 ± 0.02 | 7.2 ± 0.7 |
| corr-4e | (structure) | 0.16 ± 0.01 | 6.9 ± 0.5 |
| Class 5: 2-(N-phenylamino)quinolines | | | |
| corr-5a | (structure) | 0.17 ± 0.01 | 13 ± 1 |
| corr-5b | (structure) | 0.15 ± 0.02 | 15 ± 3 |
| corr-5c | (structure) | 0.15 ± 0.01 | 8.0 ± 0.4 |
| corr-5d | (structure) | 0.11 ± 0.01 | 13 ± 2 |

TABLE 1-continued

| | | $V_{max}$ (mM/s) | $K_a$ (μM) |
|---|---|---|---|
| corr-5e | 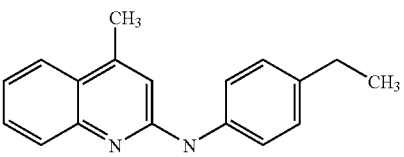 | 0.08 ± 0.01 | 8.6 ± 0.2 |
| corr-5f | 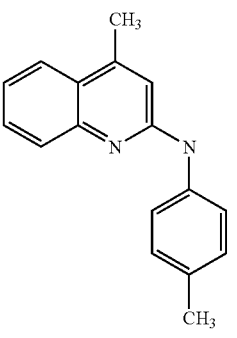 | 0.13 ± 0.01 | 8.4 ± 1.0 |
| corr-5g | 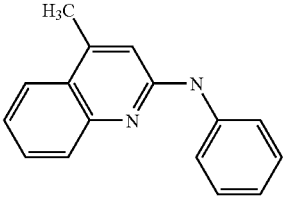 | 0.13 ± 0.02 | 10.0 ± 2.8 |
| corr-5h | 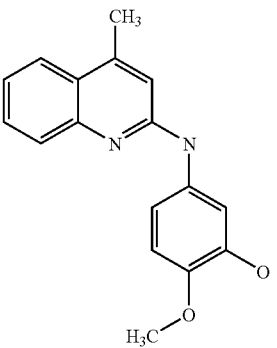 | 0.12 ± 0.01 | 7.3 ± 0.4 |

Figure 6:
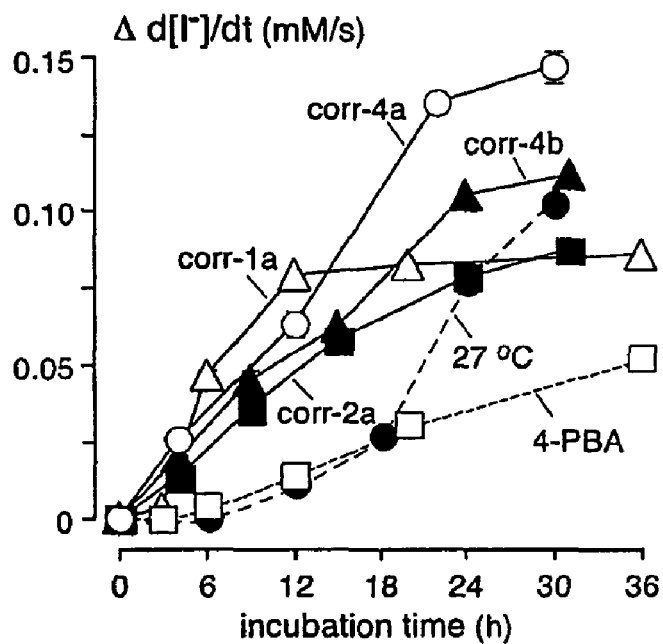
FIG. 6, panel A shows a time-course of correction with the indicated corrector compound. Cells incubated for different times at 27° C. or with indicated correctors or 4-PBA (4 mM) at 37° C. ΔF508-CFTR activity was assayed in the presence of foskolin/genistein. Panel B shows persistence of correction with the indicated corrector compound. Cells were incubated for 24 hours with the indicated corrector compounds (or 27° C.). ΔF508-CFTR activity was assayed at different times after washout (or return from 27° C. to 37° C.).
Figure 6:
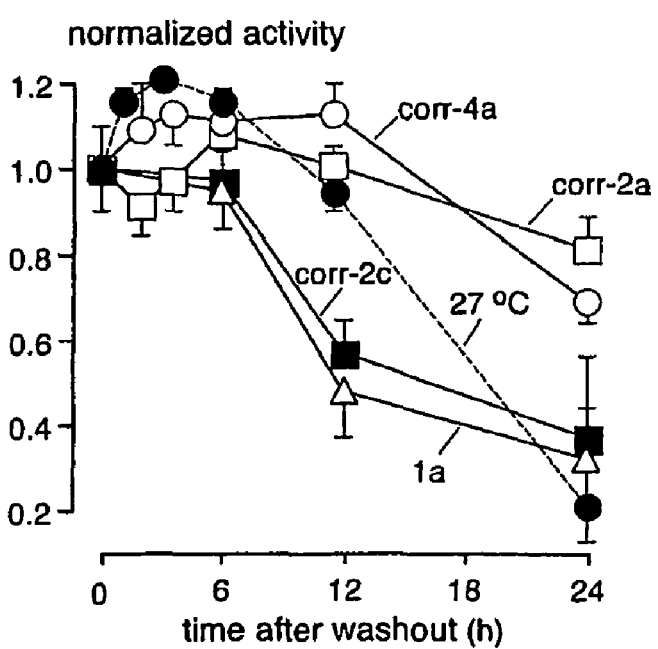

FIG. 6, panel A, summarizes the time course of correction for four corrector compounds (incubated at 37° C.), with data for 27° C. rescue and 4-PBA shown for comparison. Correction was seen as early as 3 hours after compound addition, with maximal effect after 12-30 hours. In contrast, correction by 27° C. incubation or 4-PBA had a relatively slower onset. Data for the persistence of correction after compound washout (or return of temperature from 27° C. to 37° C.) are summarized in FIG. 6, panel B. Correction persisted beyond 12 hours for most compounds after washout, with substantial activity remaining for two of the correctors at 24 hours. In contrast, little correction persisted at 24 hours for the 27° C. rescued cells.

Figure 7:
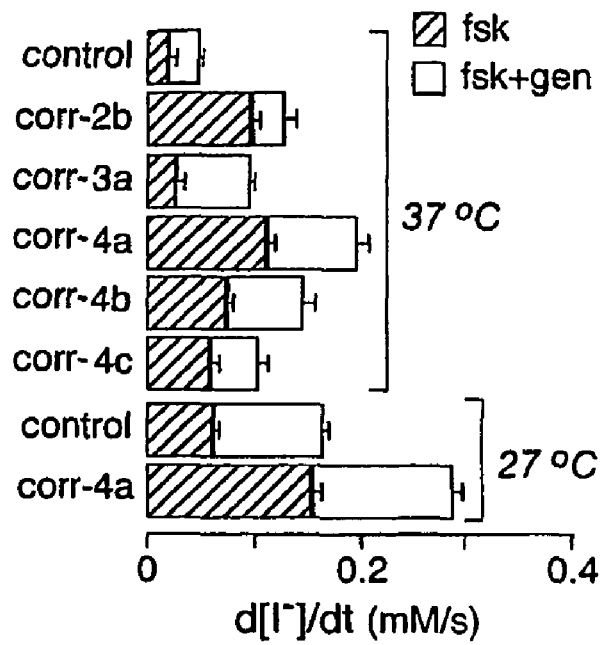
FIG. 7 shows the effect of forskolin (20 μM) or forskolin+genistein (50 μM) in cells kept at 37° C. or 27° C. with or without corrector compounds.
Figure 8:
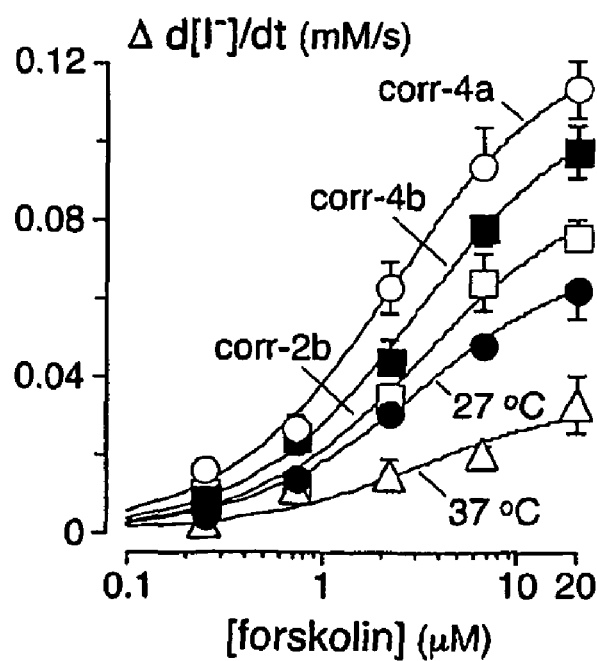
FIG. 8 is a graph showing forskolin dose-response relationships. ΔF508-CFTR expressing FRT cells were stimulated with forskolin (in the absence of genistein) after incubation with the indicated corrector compound at 37° C. or 27° C.
Figure 9:
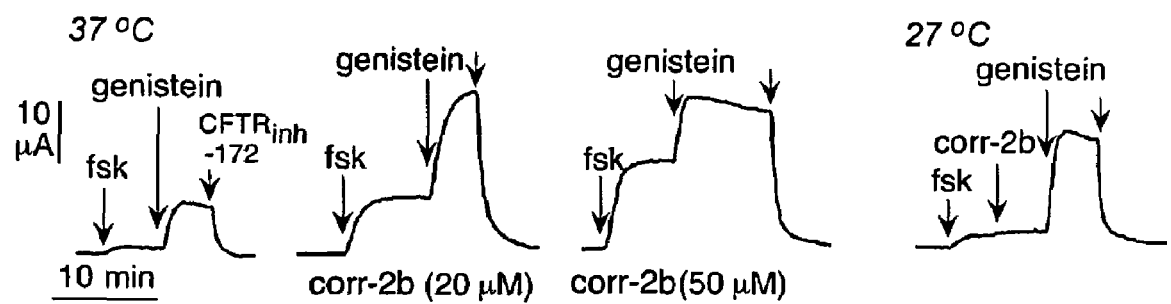
FIG. 9 shows apical membrane chloride current measurements after incubation for 24 hours at 37° C. with DMSO vehicle (left) or compound corr-2b ($2^{nd}$ and $3^{rd}$ curves). Curve at the right shows results in cells grown at 27° C. with compounds added as shown (20 μM forskolin, 20 μM corr-2b, 50 μM genistein).

Experiments were done to investigate whether the corrector compounds might alter the properties of ΔF508-CFTR, such as the sensitivity to cAMP-elevating agents or to potentiator compounds. FIG. 7 summarizes $V_{max}$ for forskolin alone (at 20 μM) vs. forskolin+genistein (50 μM). Interestingly, the fractional $V_{max}$ produced by forskolin alone vs. forskolin+genistein was greater in cells treated with correctors vs. low temperature. Thus, several corrector compounds increased ΔF508-CFTR activation by forskolin alone. Compound corr-2b was most effective, with the forskolin response representing ~80% of $V_{max}$. FIG. 8 shows forskolin dose-response data (in the absence of genistein). Although $V_{max}$ differed, $K_a$ for the forskolin response was ~3 μM in each case. As seen in Ussing chamber experiments (FIG. 9) compound corr-2b at 20 μM (and even more at 50 μm) increased the relative amplitude of the forskolin response. This was not due to intrinsic potentiator activity of compound corr-2b, as it was unable to stimulate CFTR activity in 27° C. rescued cells, with genistein as positive control (FIG. 9, right panel).

High-throughput screening produced several classes of small molecules that corrected ΔF508-CFTR cellular misprocessing and restored plasma membrane expression and halide permeability to levels greater than that achieved by low temperature rescue. Correction was verified by electrophysiological and biochemical measurements, as well as by using control (non-expressing) cells and a CFTR-selective inhibitor.

The cell line used for primary screening was chosen to be of epithelial origin (to resemble native CFTR-expressing cells), to permit rapid assessment of chloride currents in cell monolayers, and to give a robust low-temperature rescue response. Additional requirements for the cell line for high-throughput screening included rapid growth in test plates, stable and bright YFP-H148Q/I152L expression, and low basal halide permeability. The YFP-H148Q/I152L fluorescent halide indicator was developed previously (Galietta et al., FEBS Lett. 499:220-224 (2001)) as having bright cellular expression and ultra-high iodide sensitivity. The transfected FRT cell line used was selected after screening many transfected and natively-expressed epithelial cell lines, and well as more than one hundred ΔF508-CFTR/YFP-H148Q/1152L transfected FRT cell clones.

Example 2

Mechanistic Analysis of ΔF508-CFTR Correctors

Figure 10:
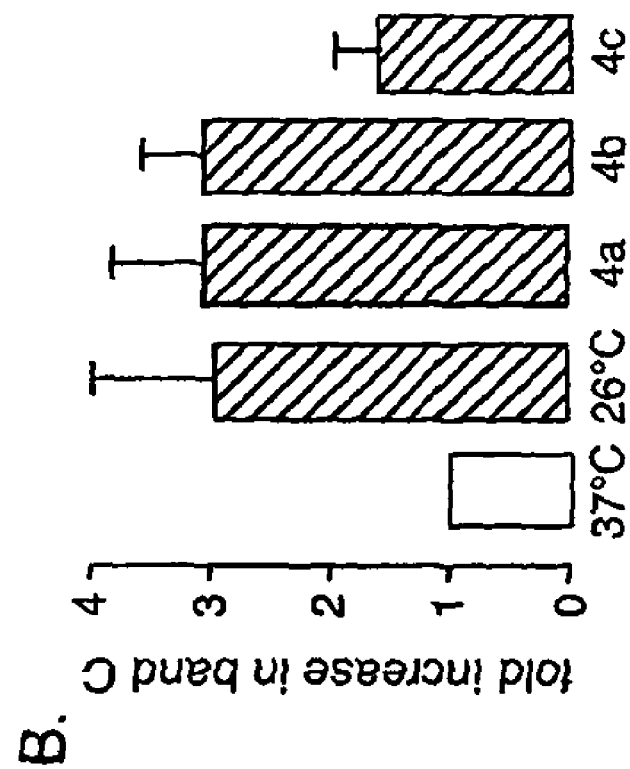
FIG. 10, panel A is a western blot showing the effect of the indicated corrector compound (10 μM) on the expression pattern of ΔF508-CFTR-C,HA in BHK cells. Where indicated cells were cultured for 24 hours at 37° C. in the absence or presence of corrector compounds, or at 27° C. CFTR was visualized by anti-HA primary and HRP-conjugated secondary antibodies by enhanced chemiluminescence. Filled arrowhead, complex-glycosylated forms (band C), empty arrowhead, core-glycosylated form (band B). Panel B is a graph showing the quantification of the data in panel A.
Figure 10:
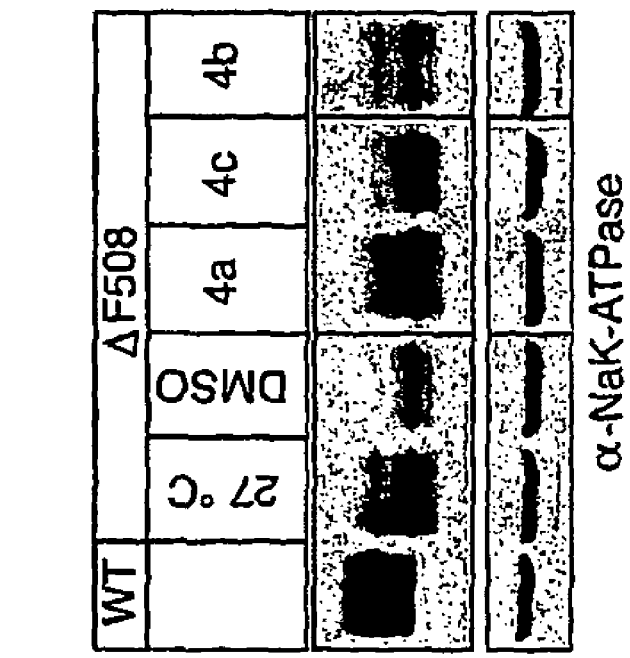
Figure 11:
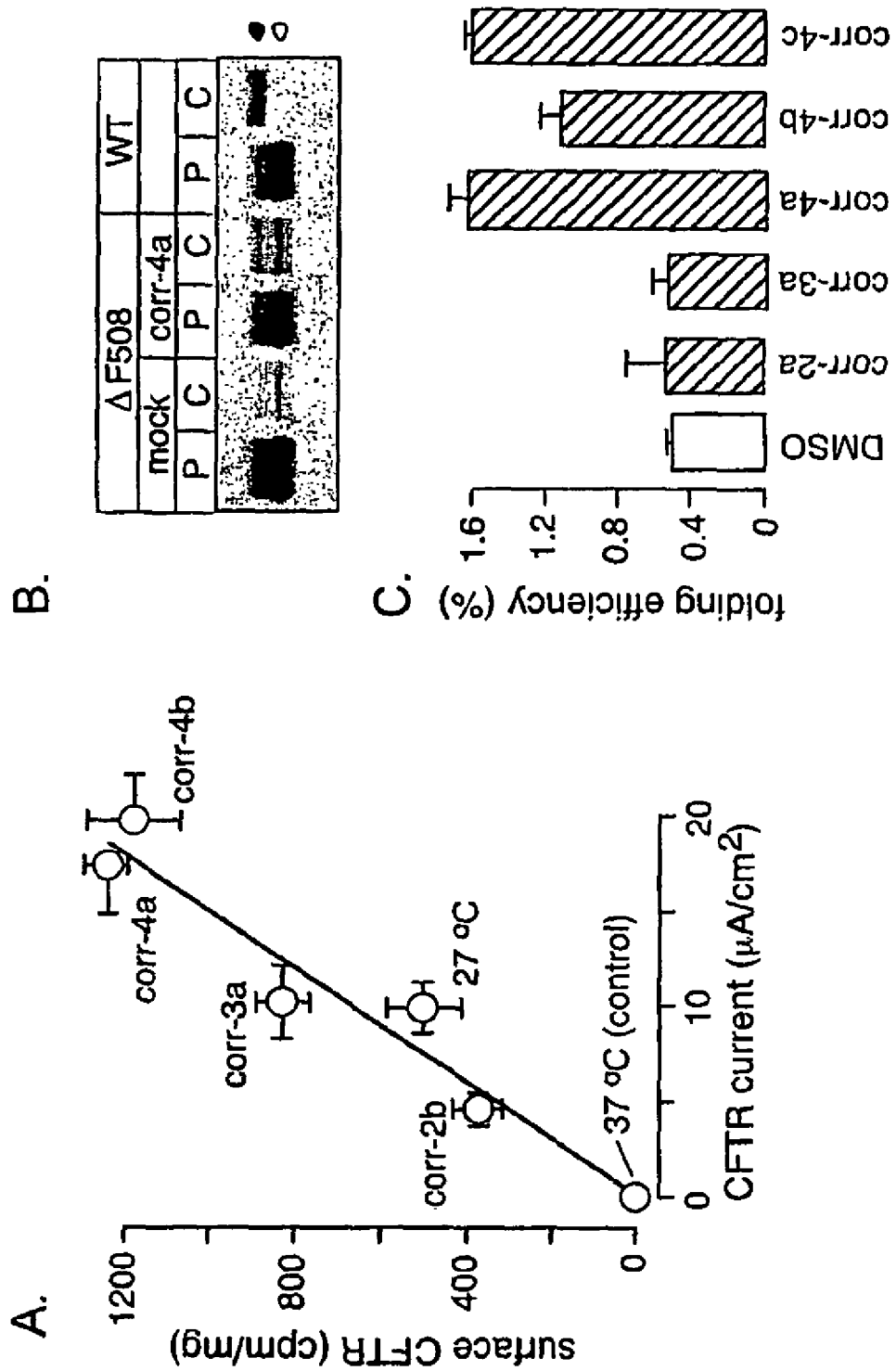
FIG. 11, panel A is a graph showing cell surface density of ΔF508-CFTR determined using the radioactive anti-HA antibody binding assay for condition as in FIG. 10, panel A, plotted against ΔF508-CFTR apical membrane currents in parallel experiments done in FRT cells. Panel B is a western blot showing the folding efficiency measured by pulse-chase analysis. Translation rate computed from radioactive incorporation during a 15 min pulse (P). To measure the folding efficiency, cells were pulse for 150 min and than chased for 120 min (C). The amount of core-(empty arrowhead) and complex-glycosylated (filled arrowhead) form was determined by phosphorimage analysis. Panel C is a graph showing maturation efficiency expressed as the percent of mature, complex-glycosylated ΔF508-CFTR relative to the pulse-labeled pool as shown in panel B.

To provide biochemical evidence for the biosynthetic processing of ΔF508-CFTR in the presence of correctors, the accumulation of mature, complex-glycosylated ΔF508-CFTR-$C_t$HA was monitored by immunoblot analysis in baby hamster kidney (BHK) cells. Incubation of cells with correctors for 16-24 hours at 37° C. resulted in the accumulation of complex-glycosylated ΔF508-CFTR (FIG. 10, panel A). This was evidenced by the slower electrophoretic mobility (apparent M.W. ~170 kDa) of the complex-glycosylated ΔF508-CFTR immunoreactive band, compared to its core-glycosylated counterpart (apparent M.W. ~150 kDa), the predominant form in non-treated cells. Similar results were obtained in ΔF508-CFTR expressing FRT cells. The accumulation of the complex-glycosylated ΔF508-CFTR in corrector-treated cells was comparable to that produced by low temperature incubation without correctors (FIG. 10, panel B). The corrector compounds did not produce an ER stress response based on the unaltered expression level of the ER chaperone Grp78. Plasma membrane ΔF508-CFTR expression was confirmed using an anti-HA antibody binding assay based on the recognition of an extracellular epitope (Ma et al., JBC 277:37235-37241 (2002)). Incubation with corrector compounds increased the abundance of plasma membrane ΔF508-CFTR significantly, with an approximately proportionate increase in forskolin/genistein-stimulated apical membrane chloride current (FIG. 11, panel A).

Figure 12:
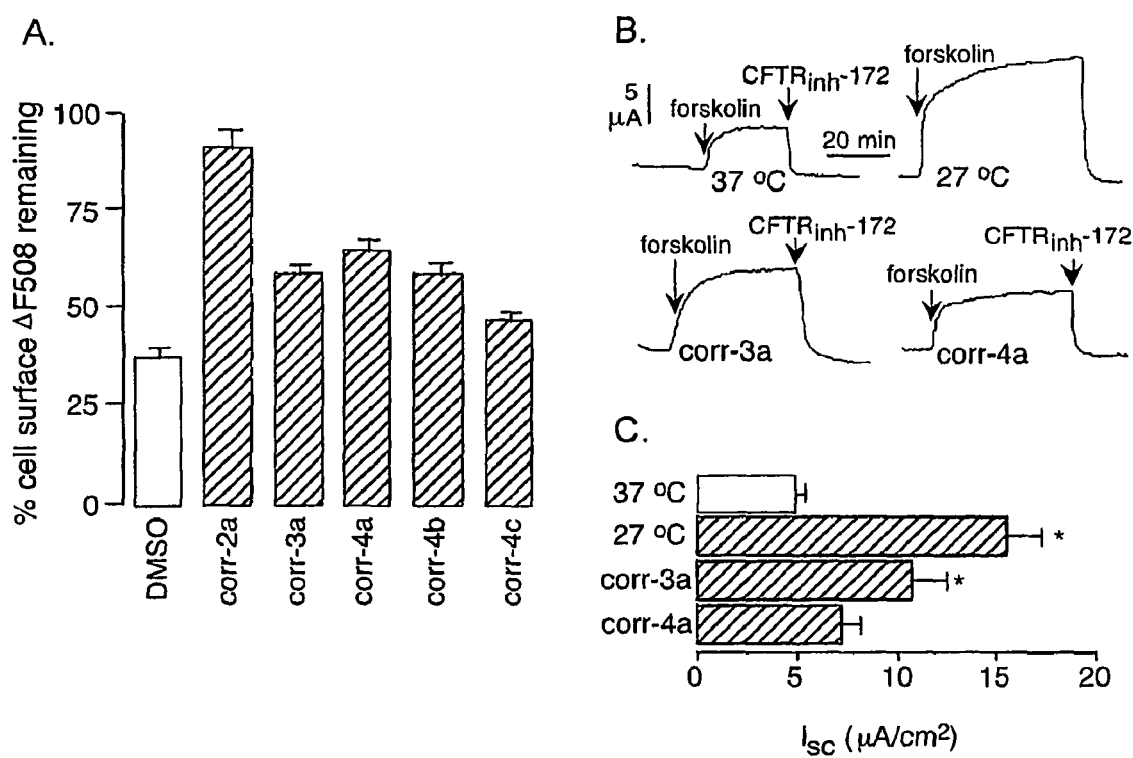
FIG. 12, panel A, is a graph showing cell surface stability of the rescued ΔF508-CFTR as measured by the anti-HA antibody-binding assay before and after 3 hours of chase in the presence of the indicated corrector compound. Panel B shows results of apical membrane chloride current in FRT cells expressing the temperature-sensitive mutant P574H-CFTR. Panel C is graph showing the results of the apical membrane chloride current study of Panel B.

The ΔF508 mutation impairs the ΔF508-CFTR conformational maturation and export competence of the channel at the endoplasmic reticulum, and destabilizes the complex-glycosylated ΔF508-CFTR in post-Golgi compartments (Sharma et al., 2001; Sharma et al., 2004). Corrector compounds may thus facilitate the posttranslational folding of newly synthesized ΔF508-CFTR as well as enhance the stability of mature, complex-glycosylated ΔF508-CFTR. To establish the cellular basis of corrector action, corrector effects on ΔF508-CFTR post-translational folding efficiency was quantified by the metabolic pulse-chase technique, measuring the fractional conversion of newly synthesized, core-glycosylated ΔF508-CFTR into the complex-glycosylated form (FIG. 11, panel B). By extending the radioactive pulse-labeling from 15 to 150 minutes, the detection sensitivity of the assay was significantly increased. Phosphorimage analysis showed that ΔF508-CFTR has low, but measurable maturation efficiency (0.5±0.15%) as compared to the wildtype CFTR (31±5%) in BHK cells at 37° C. Similar results were obtained for maturation efficiency of wildtype CFTR in other heterologous expression systems (Ward et al., 1994; Lukacs et al., EMBO J. 13:6076-6086 (1994)). ΔF508-CFTR folding efficiency was increased by 2-3 fold in the presence of some corrector compounds (FIG. 11, panel C). Next, ΔF508-CFTR-3HA cell surface stability was assessed. ΔF508-CFTR-3HA was first accumulated at the cell surface at reduced temperature (as in FIG. 10, panel A). Then the temperature was increased to 37° C. in the presence of correctors and ΔF508-CFTR stability was monitored by the disappearance of anti-HA bound to the channel at 4° C. While the cell surface density of rescued ΔF508-CFTR decreased to ~20% during the 3 hours chase, 50-90% of the ΔF508-CFTR protein remained at the cell surface in the presence of corrector compound (FIG. 12, panels B and C). Thus, the corrector compounds also enhance the residence time of the rescued ΔF508-CFTR protein at the cell surface.

As an initial test of compound specificity for correction of defective ΔF508-CFTR misprocessing, compounds were tested on P574H-CFTR, a mutant CFTR that similar to ΔF508-CFTR is retained at the endoplasmic reticulum but can be rescued by incubation for 24 hours at reduced temperature (Ostedgaard et al., J. Cell Sci., 112:2091-2098 (1999)). Cells were incubated with correctors or at reduced temperature for 24 hours. Apical membrane chloride current was measured in response to forskolin (which fully activates this CFTR mutant, Sheppard et al., EMBO J. 14:876-883 (1995)) and then $CFTR_{inh}$-172. FIG. 12 shows that corr-4a compound, which produced robust chloride currents in ΔF508-CFTR expressing cells, had no effect on the P574H-CFTR cells, despite a positive low temperature rescue control. Corr-3a compound produced a two-fold increase in chloride current.

CFTR cellular processing involves translation, folding at the ER, Golgi transport, post-translational glycosylation, and apical plasma membrane targeting. Plasma membrane CFTR is internalized by endocytosis, and then recycled to the plasma membrane or targeted for lysosomal degradation (Sharma et al., 2004; Gentzsch et al., MBC 5:2684-2696 (2004)). ΔF508-CFTR folding is inefficient. In BHK cells with 99.5% of newly synthesized ΔF508-CFTR in BHK cells targeted for degradation without reaching the Golgi. Near complete ER retention of ΔF508-CFTR was reported in other model systems as well. Corr-4b and corr-4c compounds increased ΔF508-CFTR folding efficiency nearly 3-fold without effect on translational rate, suggesting that the corrector compounds could partially overcome the post-translational folding barrier. Based on recent structural studies it is conceivable that small molecules can facilitate the folding of the NBD2 and/or transmembrane domains (Du et al., Nat. Struct. Biol., 2005, Chen et al., JBC 279:39620-39627 (2004)). The simplest interpretation of the peripheral stabilizing effect of the correctors is that the conformationally stabilized mutant is less susceptible to the ubiquitin-dependent peripheral quality control mechanism and lysosomal degradation than the rescued ΔF508-CFTR in the absence of corrector compounds (Sharma et al., 2004).

Example 3

ΔF508-Correction in Human Airway Epithelium

Figure 13:
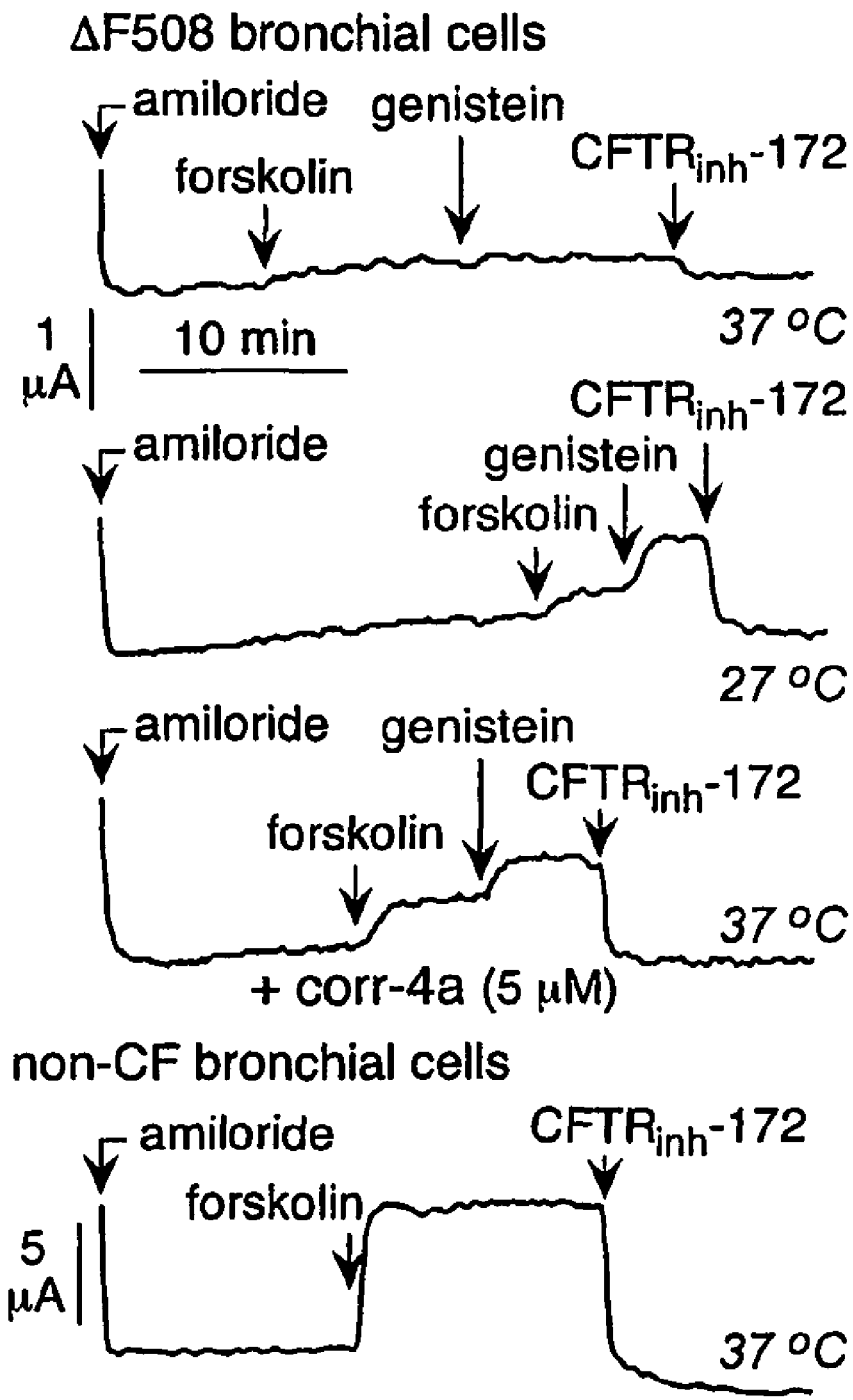
FIG. 13 shows representative short-circuit current recordings on primary cultures of human airway epithelial cells from a ΔF508 homozygous subject (top 3 curves) and non-CF subject (bottom curve). ΔF508 cells maintained at 37° C. for 24 hours in the presence of DMSO vehicle or compound corr-4b, or incubated at 27° C. Concentrations: amiloride (10 μM), forskolin (20 μM), genistein (50 μM), $CFTR_{inh}$-172 (10 μM).
Figure 14:
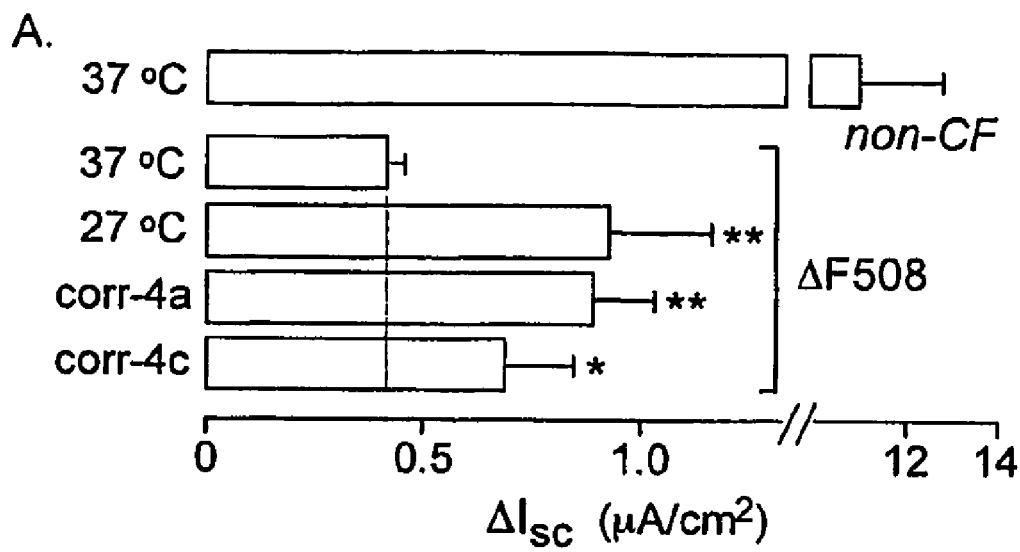
FIG. 14, panel A is a summary of $CFTR_{inh}$-172 inhibitable short-circuit current ($\Delta I_{sc}$) for a series of experiments as in FIG. 13 (SE, n=12-14). *, P<0.05, **, P<0.01. Panel B shows short-circuit current recordings of primary cultures of human bronchial epithelial cells from a homozygous N1303K-CFTR subject done under conditions as in FIG. 13.
Figure 14:
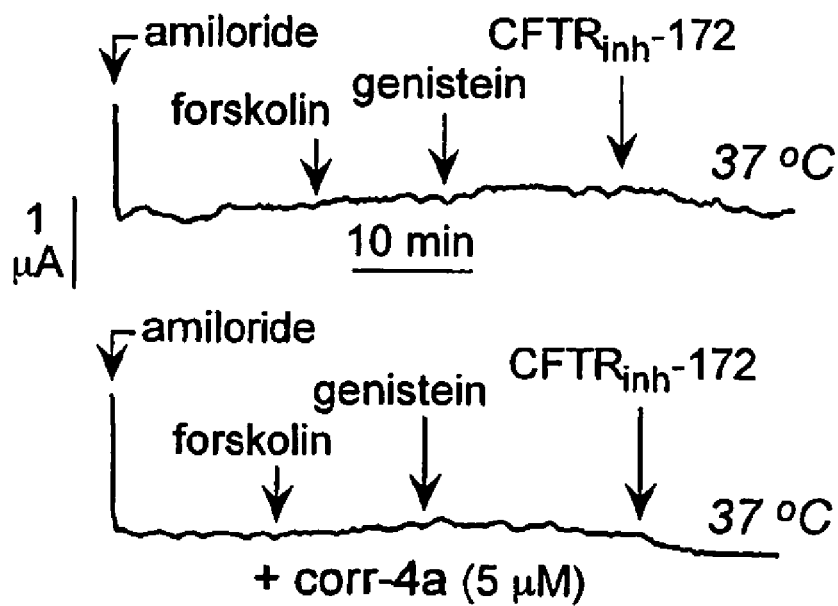

The corrector compounds were also tested on differentiated primary cultures of human airway epithelial cells from ΔF508-CFTR homozygous subjects. Cells polarized on permeable supports were mounted in Ussing chambers for measurement of chloride secretion by short-circuit current analysis. After blocking Na⁺ current with amiloride, cells treated with DMSO vehicle alone showed little response to forskolin, genistein, or CFTR$_{inh}$-172 (FIG. 13). Incubation at 27° C. for 24 hours resulted in the appearance of significant chloride current as seen by the increased current after forskolin and genistein, and the inhibition by CFTR$_{inh}$-172. The results show that incubation with the compound corr-4a at 37° C. for 24 hours increased chloride current comparably. For comparison, data for non-CF bronchial epithelial cells are shown (FIG. 13, bottom panel). FIG. 14, panel A, summarizes the changes in short-circuit current produced by CFTR$_{inh}$-172 inhibition for a series of measurements as in A, including data for a second bisaminomethylbithiazole. As a negative control for these studies, the same corrector compounds were tested on human bronchial epithelial cells derived from a subject homozygous for the N1303K-CFTR mutation, which also manifests defective CFTR processing (Gregory et al., MCB 11:3886-3893 (1991)). FIG. 14, panel B, shows no significant correction of short-circuit current for the N1303K-CFTR bronchial cells when measured with the same compounds and conditions used for the ΔF508-CFTR cells in FIG. 13.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently Icnown equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A pharmaceutical composition comprising a compound of formula (IV):

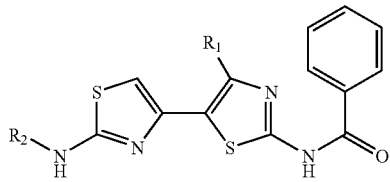

wherein R$_1$ is a alkyl group and R$_2$ is a substituted or unsubstituted phenyl group; or a pharmaceutically acceptable derivative thereof, as an individual stereoisomer or a mixture thereof; or a pharmaceutically acceptable salt thereof.

2. The pharmaceutical composition of claim 1, wherein the composition further comprises at least one of a pharmaceutically acceptable carrier, a pharmaceutically acceptable diluent, a pharmaceutically acceptable excipient and a pharmaceutically acceptable adjuvant.

3. The pharmaceutical composition of claim 1, wherein the composition does not contain detectable dimethyl sulfoxide.

4. The pharmaceutical composition of claim 1, wherein R$_1$ is a methyl group.

5. The pharmaceutical composition of claim 1, wherein R$_2$ is chosen from a 3-(nitro)phenyl group, a 2-methoxyphenyl, a 2-ethoxyphenyl, a 1-phenylethyl-1-one group, or a 3-chloro-6-methoxyphenyl group.

6. The pharmaceutical composition of claim 1, wherein the compound is chosen from:

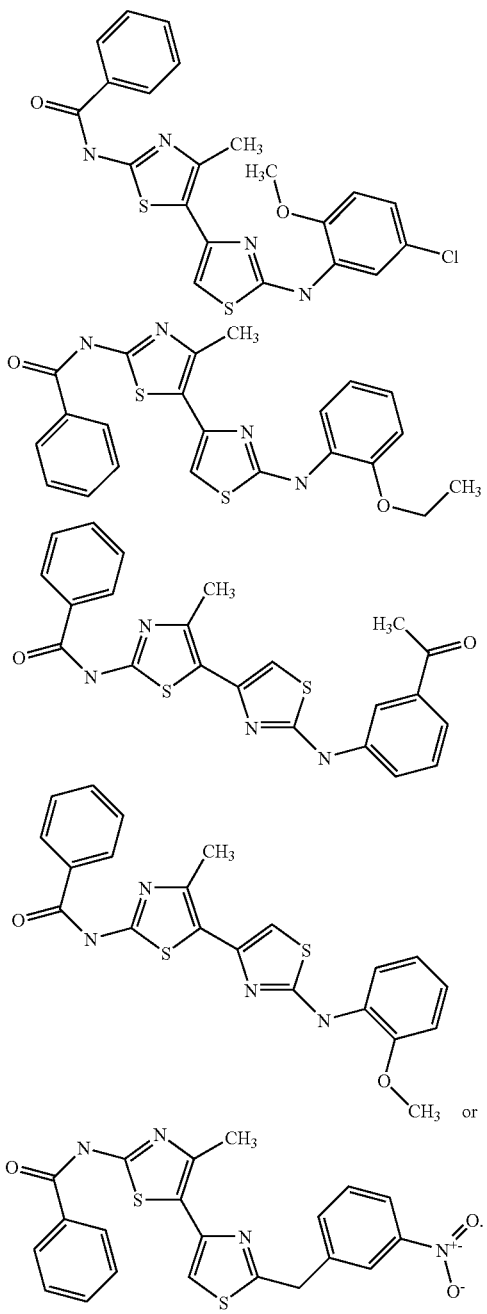

7. A method of treating a subject having a condition associated with mutant-CFTR, said method comprising administering to the subject a therapeutically effective amount of a pharmaceutical composition of claim 1.

8. The method of claim 7, wherein said condition is cystic fibrosis.

9. The method of claim 7, wherein the subject, after treatment, has a decrease in mucous or bacterial titer in their lungs, a decrease in coughing or wheezing, a decrease in pancreatic insufficiency, or a decrease in electrolyte levels in their sweat.

10. The method of claim 7, wherein said subject is a non-human animal.

11. The method of claim 7, wherein the animal is a mammal.

12. The method of claim 7, wherein the mutant-CFTR is a ΔF508-CFTR.

* * * * *